(12) United States Patent
Nishi et al.

(10) Patent No.: US 6,413,695 B1
(45) Date of Patent: Jul. 2, 2002

(54) RESIST COMPOSITIONS AND PATTERNING PROCESS

(75) Inventors: Tsunehiro Nishi; Takeshi Kinsho; Takeru Watanabe; Koji Hasegawa; Mutsuo Nakashima; Jun Hatakeyama, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/572,973

(22) Filed: May 18, 2000

(30) Foreign Application Priority Data

May 19, 1999 (JP) .......................................... 11-138086

(51) Int. Cl.$^7$ ............................................. G03F 7/004
(52) U.S. Cl. ...................... 430/270.1; 430/296; 430/325
(58) Field of Search ............................. 430/270.1, 325, 430/296

(56) References Cited

U.S. PATENT DOCUMENTS

| | | | | |
|---|---|---|---|---|
| 6,030,746 A | | 2/2000 | Nagata et al. ........... | 430/270.1 |
| 6,048,661 A | | 4/2000 | Nishi et al. .............. | 430/270.1 |
| 6,238,842 B1 | * | 5/2001 | Sato et al. ............... | 430/281.1 |
| 6,265,131 B1 | * | 7/2001 | Chang et al. ............ | 430/270.1 |

FOREIGN PATENT DOCUMENTS

| | | |
|---|---|---|
| EP | 0 646 568 | 4/1995 |
| EP | 0 918 048 | 5/1999 |
| JP | 6-266109 | 9/1994 |
| JP | 9-278699 | 10/1997 |

OTHER PUBLICATIONS

127: 364169 CA abstract of JP 09–265177, Oct. 1997.*
Translation of JP 09–265177, 10–1997 (machine translation at www.ipdl.jpo.go.jp/homepg$_{13}$e.ipdl).*
Janusz J M et al: "High Potency Dipeptide Sweetners. 1. L–Aspartly–D–Phenylglycine Esters" Journal of Medicinal Chemistry, American Chemical Society, vol. 13, No. 3, Mar. 1, 1990 pp. 1052–1061.
Banert K et al: Chemische Berichte., vol. 116, No. 11,1983, pp. 3591–3610.
Brown H C et al: Journal of the American Chemical Society., vol. 90, No. 10, 1968 pp. 2691–2693.
Roberts J D et al: Journal of the American Chemical Society., vol. 75, 1953 pp. 3165–3168.
Johansson A et al: "A Short and Selective Synthesis of (S)–Geranylcitronllol Via Conjugate Addition of a Functionalized Copper Reagent to 2–Substituted Exo–Bornyl Crotonates" Tetrahedron Letters, NL, vol. 37, No. 39 Sep. 23, 1996.
Bergdahl M et al.: Tetrahedron, vol. 47, No. 46, 1991, pp. 9691–9702.
Olsson T et al: Tetrahedron., vol. 46, No. 7, 1990, pp 2473–2482.
Olsson T et al: Journal of Organic Chemistry., vol. 53, No. 11, 1988, pp. 2468–2472.
Bohlman C et al: Liebigs Annalen Der Chemie., vol. 9, 1985, pp 1752–1763.
Huckel; Justus Liebigs Annalen Der Chemie., vol. 549, 1941, 186–208.
Huckel et al; Justus Liebigs Annalen Der Chemie., vol. 585, 1954, 182–208.
Chemical Abstracts, vol. 119, No. 4, Jul. 26, 1993 Chen et al; pp. 413.
Chemical Abstracts, vol. 118, No. 3, Jan. 18, 1993 Popova et al; pp. 711.
Ludwick A G et al; Journal of Organic Chemistry, vol. 34, 1969, pp. 4108–4115.
Toivonen N J et al: Anales Academiae Scientiarum Fennicae Series A II, vol. 64, 1955, pp. 3–11 Helsinki Finland.
English Abstract for JP 6–266109.
Chemical AbstEnglish Abstract, 30—Terpenes, 1993, p. 711, vol. 118.

* cited by examiner

*Primary Examiner*—Rosemary Ashton
(74) *Attorney, Agent, or Firm*—Millen, White, Zelano & Branigan, P.C.

(57) ABSTRACT

A resist composition comprising an exo-form 2-alkylbicyclo[2.2.1]heptan-2-yl ester compound as a dissolution regulator has a high sensitivity, resolution, etching resistance and storage stability and lends itself to micropatterning with electron beams or deep-UV rays.

15 Claims, No Drawings

RESIST COMPOSITIONS AND PATTERNING PROCESS

BACKGROUND OF THE INVENTION

1. Field of the Invention

The present invention relates to a resist composition, preferably of the chemical amplification type, especially of the chemical amplification positive type, and a patterning process using the same.

2. Prior Art

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with KrF excimer lasers, polyhydroxystyrene having a practical level of transmittance and etching resistance is, in fact, a standard base resin. For resist materials for use with ArF excimer lasers, polyacrylic or polymethacrylic acid derivatives and polymers comprising aliphatic cyclic compounds in the backbone are under investigation. In either case, the basic concept is that some or all of alkali soluble sites of alkali soluble resin are protected with suitable acid-eliminatable groups. The overall performance of resist material is adjusted by a choice from among a variety of acid-eliminatable protective groups or by incorporating one or more low-molecular-weight components having an appropriate function separate from the resin.

One typical functional low-molecular-weight component to be formulated in resist materials is a class of compounds known as dissolution regulators. A variety of proposals have been made on the structure of dissolution regulators. A common structure has on a mother nucleus of a certain size one or plural readily alkali-soluble sites, some or all of which are blocked with acid-decomposable protective groups (see JP-A 6-266109 and JP-A 9-278699). When an appropriate amount of dissolution regulator is blended, the dissolution of the resist film in the unexposed area is restrained whereas in the exposed area, readily alkali-soluble sites which are exposed under the action of generated acid promote the dissolution of the resist film. That is, the differential dissolution rate between the exposed and unexposed areas is enhanced. Consequently, the resolution of the resist film is considerably improved.

What is required for the dissolution regulator is to keep low the dissolution rate of the resist film in the unexposed area and to allow the exposed area to quickly turn to be readily soluble in an alkali developer. These properties are largely affected by the mother nucleus and the choice of acid-decomposable sites. For the mother nucleus, sufficient hydrophobicity is essential for exerting dissolution inhibition in the unexposed area, and the mother nucleus must also have such a structure that developer affinity is insured in deblocked form for exerting dissolution promotion in the exposed area. Also, the acid-decomposable sites are required to have contradictory properties in that the acid-decomposable sites must have a high reactivity sufficient to quickly decompose even in low exposed area such as resist film deep inside, whereas they must have a low reactivity sufficient to prevent reaction from being triggered merely by exposure and a stability sufficient to prevent a sensitivity variation during storage, in order to restrain the formation of volatile decomposition products which can contaminate the optical system of an aligner. As to the mother nucleus, it is relatively easy to design the mother nucleus having hydrophobicity and developer affinity upon deblocking adequate to the purpose, by increasing the molecular weight above a certain level and optionally incorporating a cyclic structure. However, the acid-decomposable sites that fully satisfy the requirement are not yet available.

As to the currently available acid-decomposable sites, tertiary alkyl esters such as tert-butyl esters and 1-alkoxyalkyl esters such as 2-tetrahydropyranyl esters and 1-ethoxyethyl esters are known as the protected carboxylic acid; tertiary alkyl carbonates such as tert-butyl carbonate, tertiary alkyl ethers such as tert-butyl ethers, and 1-alkoxyalkyl ethers such as 2-tetrahydropyranyl ethers and 1-ethoxyethyl ethers are known as the protected phenolic hydroxyl group. Among the foregoing examples, however, the 1-alkoxyalkyl esters and 1-alkoxyalkyl ethers are excessively reactive and have the risk of causing contamination of the aligner optical system and sensitivity variation. Inversely, the remaining examples are poorly reactive and fail to fully accelerate the dissolution rate in the exposed area. In addition, many other proposals have been made on the acid-decomposable sites although they are not satisfactory in both reactivity and stability. While the pattern rule is increasingly scaled down, there is a need to have a dissolution regulator having improved acid-decomposable sites and a high sensitivity, high resolution resist material which can be realized thereby.

SUMMARY OF THE INVENTION

Therefore, an object of the present invention is to provide a resist composition comprising a dissolution regulator having both high reactivity and sufficient storage stability. Another object is to provide a process for forming a pattern using the same.

It has been found that an ester compound of the following general formula (1) obtained by a method to be described later is useful as a dissolution regulator to be blended in a resist composition. The resist composition having the ester compound blended therein has high sensitivity and resolution and is suited for precise microfabrication.

The invention provides a resist composition comprising an ester compound of the following general formula (1).

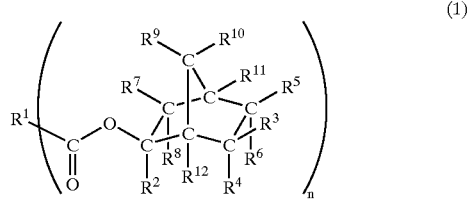

(1)

Herein $R^1$ is an n-valent straight, branched, cyclic, saturated or unsaturated hydrocarbon group of 4 to 40 carbon atoms which may contain a hetero atom. $R^2$ is a straight, branched or cyclic alkyl group of 1 to 8 carbon atoms or a substituted or unsubstituted aryl group of 6 to 20 carbon atoms. $R^3$ to $R^{12}$ each are hydrogen or a monovalent hydrocarbon group of 1 to 15 carbon atoms which may contain a hetero atom and $R^3$ to $R^{12}$, taken together, may form a ring, and when they form a ring, they represent divalent hydrocarbon groups of 1 to 15 carbon atoms which may contain a hetero atom, or two of $R^3$ to $R^{12}$ which are attached to adjacent carbon atoms may directly bond together to form a double bond. The letter n is an integer of 1 to 8. The formula also represents an enantiomer.

Preferably in formula (1), $R^1$ is an n-valent hydrocarbon group of 4 to 40 carbon atoms, in which n hydrogen atoms at arbitrary positions are eliminated to introduce valence bonds, selected from among (i) straight or branched aliphatic saturated hydrocarbons of 4 to 30 carbon atoms and alicyclic saturated hydrocarbons including

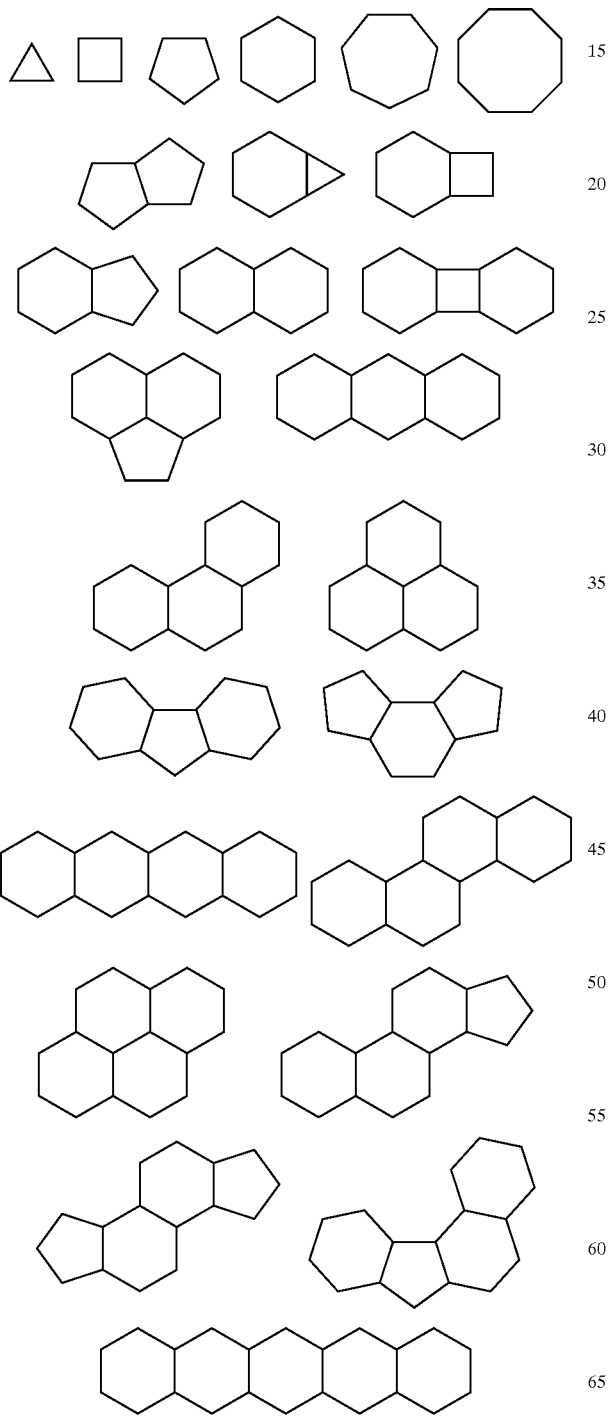

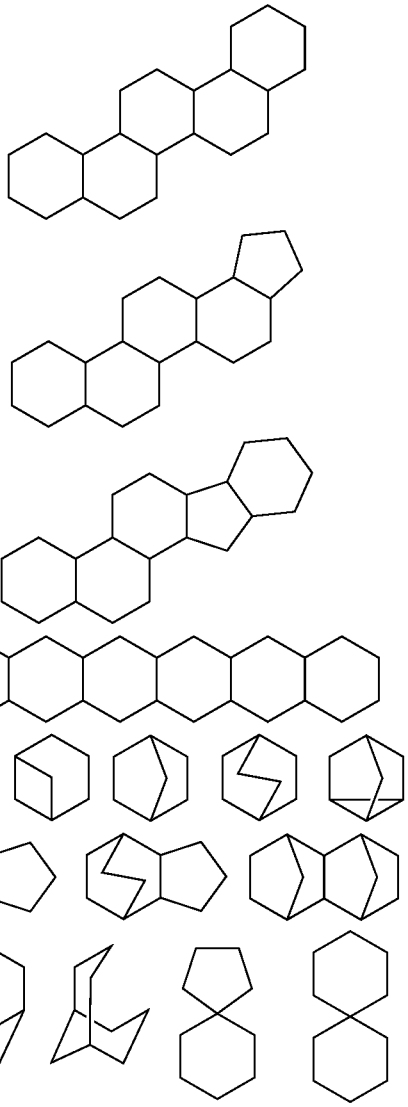

-continued (ii) hydrocarbons belonging to (i) in which at least one hydrogen atom at an arbitrary position is replaced by a straight, branched or cyclic alkyl, (iii) hydrocarbons belonging to (i) and (ii) in which a carbon-carbon bond at an arbitrary position is unsaturated to introduce at least one double or triple bond, (iv) hydrocarbons belonging to (i) to (iii) in which at least one $CH_2$, CH or C at an arbitrary position is replaced by O, N, NH, S, SO or $SO_2$, and (v) hydrocarbons belonging to (i) to (iv) in which at least one hydrogen atom at an arbitrary position is replaced by a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group or an alkyl or aryl containing said group of atoms;

$R^2$ is a straight, branched or cyclic alkyl group of 1 to 8 carbon atoms or an aryl group of 6 to 20 carbon atoms which may be substituted with an alkyl group;

$R^3$ to $R^{12}$ are independently hydrogen, or straight, branched or cyclic alkyl groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, a pair of $R^3$ and $R^4$, a pair of $R^3$ and $R^5$, a pair of $R^4$ and $R^6$, a pair of $R^5$ and $R^6$, a pair of $R^5$ and $R^7$, a pair of $R^5$ and $R^{10}$, a pair of $R^5$ and $R^{11}$, a pair of $R^6$ and $R^8$, a pair of $R^6$ and $R^{11}$, a pair of $R^7$ and $R^8$, a pair of $R^7$ and $R^9$, a pair of $R^7$ and $R^{11}$, a pair of $R^8$ and $R^{11}$, a pair of $R^9$ and $R^{10}$, a pair of $R^9$ and $R^{11}$, and a pair of $R^{10}$ and $R^{11}$ each may form a ring, and when these R's form a ring, they are independently straight, branched or cyclic alkylene groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, or a pair of $R^3$ and $R^5$, a pair of $R^5$ and $R^{11}$, a pair of $R^7$ and $R^{11}$, and a pair of $R^9$ and $R^{11}$ may form a single bond so that a double bond is formed between the carbon and the carbon to which these R's are attached.

In one preferred embodiment, the resist composition further contains a base resin, a photoacid generator (i.e., a compound capable of generating an acid upon exposure to high energy radiation or electron beams), and an organic solvent.

In another aspect, the invention provides a process for forming a pattern, comprising the steps of:
  applying the resist composition defined above onto a substrate to form a coating,
  heat treating the coating and exposing the coating to high energy radiation or electron radiation through a photomask,
  optionally heat treating the exposed coating, and developing the coating with a developer.

The ester compound of formula (1) employs an exo-form 2-alkylbicyclo[2.2.1]heptan-2-yl ester or derivative thereof as the acid-decomposable site, thereby overcoming the problems including the tert-butyl esters, tert-butyl carbonate and tert-butyl ethers having low reactivity as well as the 2-tetrahydropyranyl esters, 1-ethoxyethyl esters, 2-tetrahydropyranyl ethers and 1-ethoxyethyl ethers having excessive reactivity.

The ester compounds of formula (1) are broadly classified as alkylcycloalkyl esters. The alkylcycloalkyl esters being basically tertiary alkyl esters are free of the drawback of excessive acidolysis; when formulated into resist compositions, they do not allow reaction from taking place merely by exposure to form volatile decomposition products within the aligner or undergo decomposition during storage; nevertheless, they have higher acidolysis than simple tertiary alkyl esters such as tert-butyl esters. For these reasons, the alkylcycloalkyl esters belong to a relatively satisfactory class of acid-decomposable sites on the dissolution regulator for use in resist compositions. The ester compounds of formula (1) for use in resist compositions are successful in significantly enhancing acidolysis without compromising the advantages of the alkylcycloalkyl esters. The reason is given below.

Decomposition reaction of tertiary alkyl esters under acidic conditions proceeds by way of E1 mechanism. Those esters having a more stable carbocation under transition conditions have a higher rate of reaction and hence, a higher rate of decomposition. In the exo-form 2-alkylbicyclo[2.2.1] heptan-2-yl esters of formula (1), probably because of σ-participation, a very stable cation is formed as shown by the reaction scheme below, and thus the progress of reaction is very rapid. This is a reaction inherent to the exo-form compound of formula (1). Little or no reaction occurs with an isomer or an endo-form compound of the following formula (1'). The compounds of formulae (1) and (1'), which look alike when expressed in plan structure, have largely different rates of acid decomposition reaction. Accordingly, the compound of formula (1), the compound of formula (1'), and the compound of formula (1") expressed with no stereostructure taken into account must be recognized, in fact, to be completely different substances (see Y. Yukawa Ed., Theory of Organic Chemistry -Reaction-, Kagaku Dojin Publishing, 1974, Chap. 8).

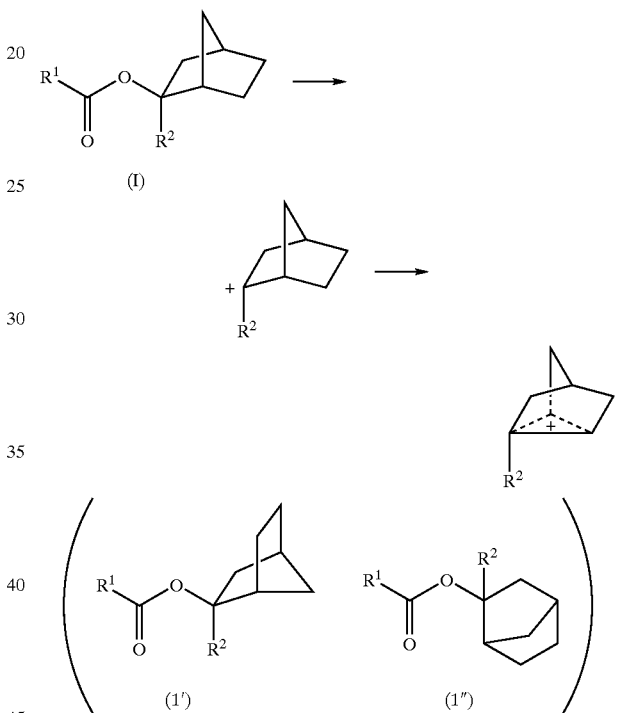

Herein, $R^1$ to $R^{12}$ and n are as defined above although $R^3$ to $R^{12}$ and n are omitted for the brevity of description.

Because of the above-described mechanism, the exo-form 2-alkylbicyclo[2.2.1]heptan-2-yl esters of formula (1) have an acid decomposition ability that outstandingly surpasses not only simple tertiary alkyl esters, but also alkylcycloalkyl esters and prior art fused ring-containing alkylcycloalkyl esters having not considered stereochemistry. Therefore, the resist composition comprising the inventive compound as a dissolution regulator becomes a very high sensitivity, high resolution resist composition as compared with prior art resist compositions, as will be later demonstrated in Examples.

Although the compounds of formula (1) have been arrived at originally from efforts in pursuit of acid decomposition, quite unexpectedly, they have some advantages in addition to high reactivity. Such advantages are a large polarity change due to the high hydrophobic nature of an eliminatable portion of the acid eliminatable site, and a very high rigidity that bicyclo[2.2.1]heptane skeleton possesses. Because of these excellent characteristics, the resist composition having blended therein the ester compound of the invention has a very high etching resistance as well as a high sensitivity and high resolution.

The ester compounds of formula (1) have been arrived at by making investigations on acid elimination reaction from the aspect of stereochemistry. In this sense, the present invention is based on a concept utterly different from the prior art improvement in acid eliminatable sites that was discussed solely from the standpoint of plane structure. The invention is clearly distinguishable from the prior art proposals of novel acid eliminatable sites.

DETAILED DESCRIPTION OF THE INVENTION

Ester Compound

The resist composition of the invention contains an ester compound of the general formula (1).

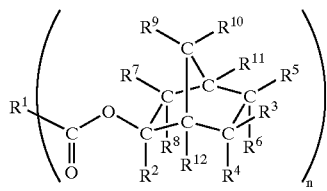

$R^1$ is an n-valent straight, branched or cyclic, saturated or unsaturated hydrocarbon group of 4 to 40 carbon atoms which may contain a hetero atom wherein n is an integer of 1 to 8.

More illustratively, $R^1$ is an n-valent $C_{4-40}$ hydrocarbon group, in which n hydrogen atoms at arbitrary positions are eliminated to introduce valence bonds, selected from among (i) straight or branched aliphatic saturated hydrocarbons of 4 to 30 carbon atoms, preferably 6 to 25 carbon atoms, more preferably 8 to 20 carbon atoms and alicyclic saturated hydrocarbons including

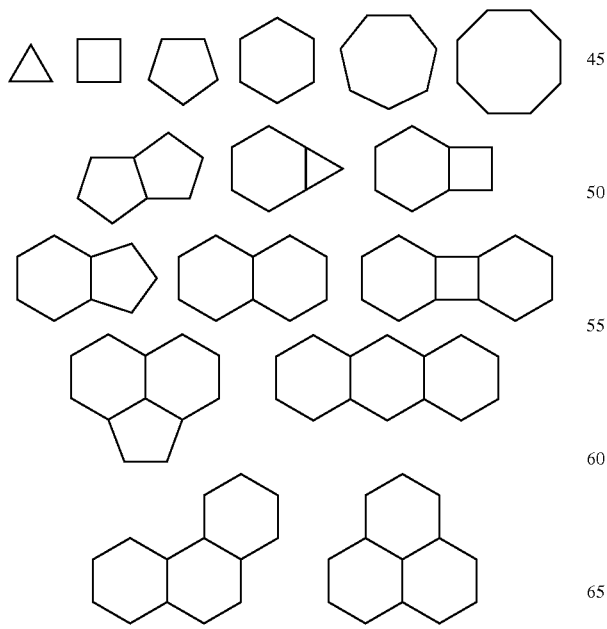

-continued

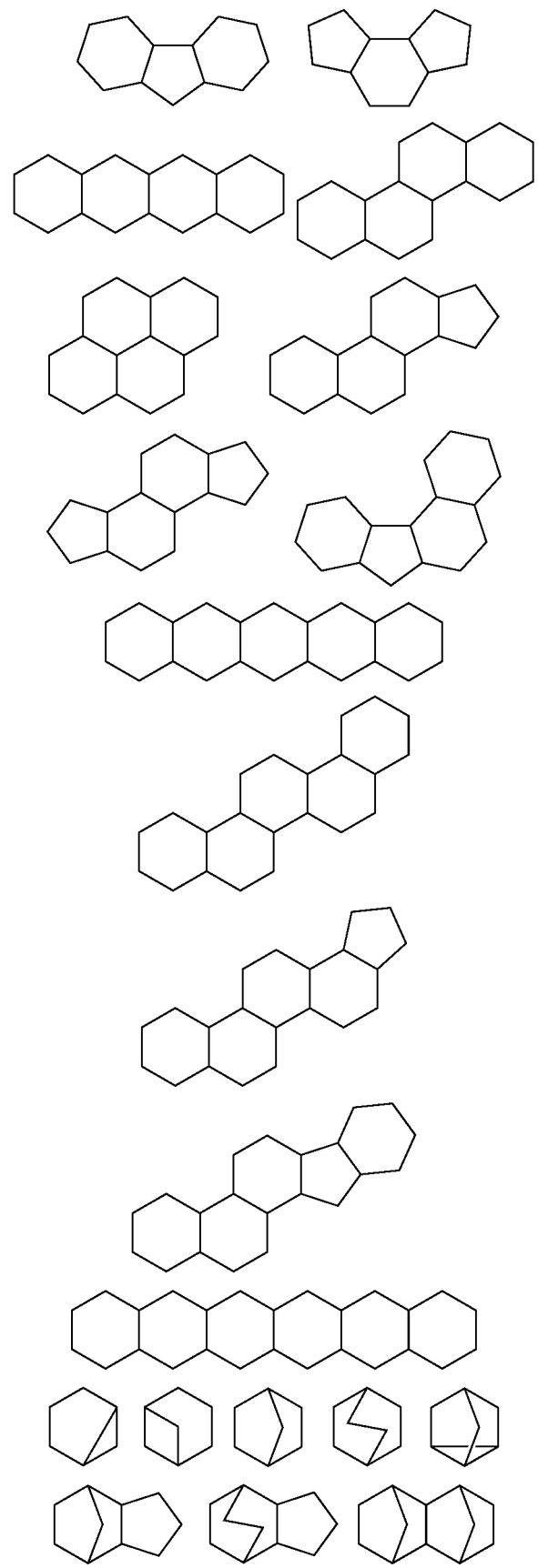

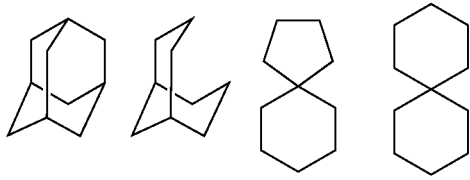

(ii) hydrocarbons belonging to (i) in which at least one hydrogen atom at an arbitrary position is replaced by a straight, branched or cyclic alkyl, preferably of 1 to 20 carbon atoms, especially 1 to 10 carbon atoms, (iii) hydrocarbons belonging to (i) and (ii) in which a carbon-carbon bond at an arbitrary position is unsaturated to introduce at least one double or triple bond, (iv) hydrocarbons belonging to (i) to (iii) in which at least one $CH_2$, CH or C at an arbitrary position is replaced by O, N, NH, S, SO or $SO_2$, and (v) hydrocarbons belonging to (i) to (iv) in which at least one hydrogen atom at an arbitrary position is replaced by a group of atoms (shown below) inclusive of a hetero atom (e.g., oxygen, nitrogen, sulfur and halogen) or an alkyl or aryl containing such a group of atoms.

As the group of atoms inclusive of a hetero atom, mention may be made of halogen atoms such as fluorine, chlorine and bromine, hydroxyl groups, alkoxy groups such as methoxy, ethoxy, butoxy and tert-butoxy, aryloxy groups such as phenyloxy, formyl groups, alkylcarbonyl groups such as methylcarbonyl and tert-butylcarbonyl, arylcarbonyl groups such as phenylcarbonyl, carboxy groups, alkoxycarbonyl groups such as methoxycarbonyl and tert-butoxycarbonyl, aryloxycarbonyl groups such as phenyloxycarbonyl, cyano groups, amino groups, alkylamino groups such as methylamino and dimethylamino, arylamino groups such as phenylamino and diphenylamino, mercapto groups, alkylthio groups such as methylthio, arylthio groups such as phenylthio, carbamoyl groups, alkylcarbamoyl groups such as dimethylcarbamoyl, arylcarbamoyl groups such as diphenylcarbamoyl, alkylcarbonylamino groups such as methylcarbonylamino, arylcarbonylamino groups such as phenylcarbonylamino, sulfo groups, oxo groups, and imino groups. Also included are alkyl groups such as methyl, ethyl and butyl and aryl groups such as phenyl, which contain any of the foregoing groups of atoms.

The group represented by $R^1$ has 4 to 40 carbon atoms, preferably 6 to 35 carbon atoms, and more preferably 8 to 30 carbon atoms as a whole.

$R^2$ is a straight, branched or cyclic $C_{1-8}$ alkyl group or a $C_{6-20}$ aryl group which may be substituted with an alkyl group. Illustrative examples of the straight, branched or cyclic alkyl group include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Illustrative examples of the unsubstituted or alkyl-substituted aryl group include phenyl, methylphenyl, naphthyl, anthryl, phenanthryl, and pyrenyl.

$R^3$ to $R^{12}$ are independently hydrogen, or straight, branched or cyclic $C_{1-15}$ alkyl groups which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group. A pair of $R^3$ and $R^4$, a pair of $R^3$ and $R^5$, a pair of $R^4$ and $R^6$, a pair of $R^5$ and $R^6$, a pair of $R^5$ and $R^7$, a pair of $R^5$ and $R^{10}$, a pair of $R^5$ and $R^{11}$, a pair of $R^6$ and R8, a pair of $R^6$ and $R^{11}$, a pair of $R^7$ and $R^8$, a pair of $R^7$ and $R^9$, a pair of $R^7$ and $R^{11}$, a pair of $R^8$ and $R^{11}$, a pair of $R^9$ and $R^{10}$, a pair of $R^9$ and $R^{11}$, and a pair of $R^{10}$ and $R^{11}$ each may form a ring. When these R's in pair form a ring, they are independently straight, branched or cyclic $C_{1-15}$ alkylene groups which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group. A pair of $R^3$ and $R^5$, a pair of $R^5$ and $R^{11}$, a pair of $R^7$ and $R^{11}$, and a pair of $R^9$ and $R^{11}$ may form a single bond so that a double bond is formed between the carbon and the carbon to which these R's are attached.

Examples of the group of atoms are the same as described for $R^1$.

In formula (1), n is an integer of 1 to 8, and preferably 1 to 6. Further preferably, n is equal to 1, 2, 3 or 4.

Illustrative examples of the ester compound according to the invention are those shown below as well as those shown in Examples though not limited thereto.

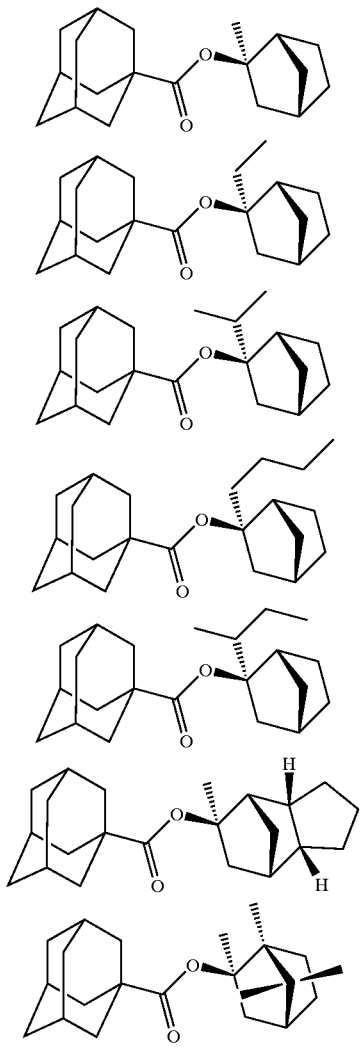

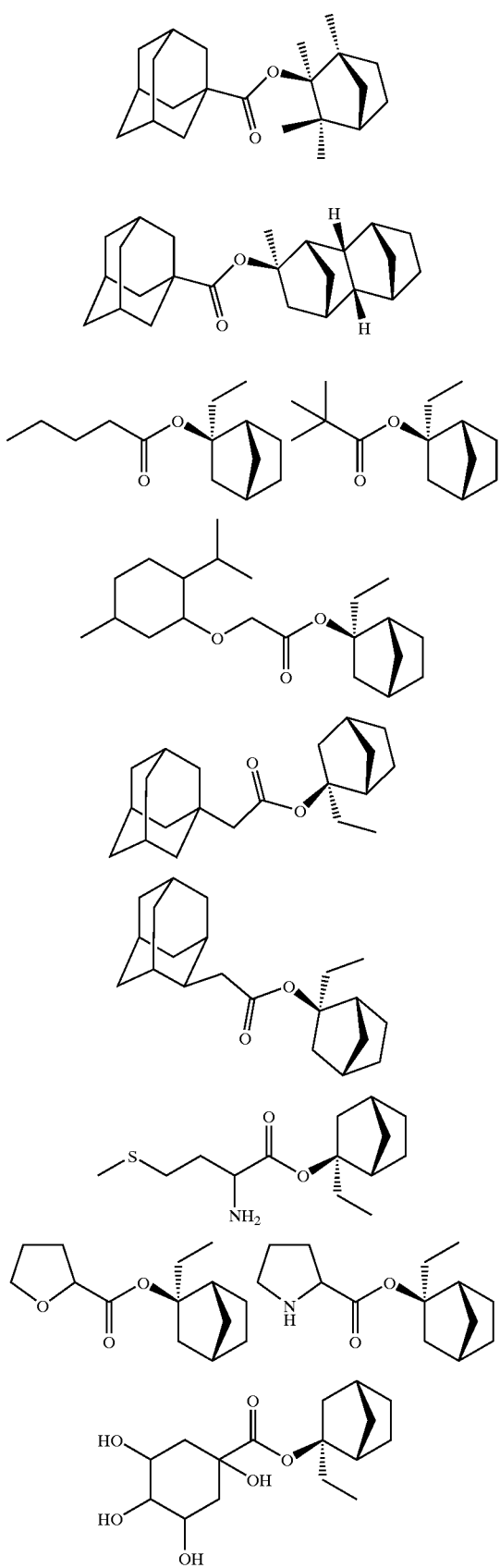
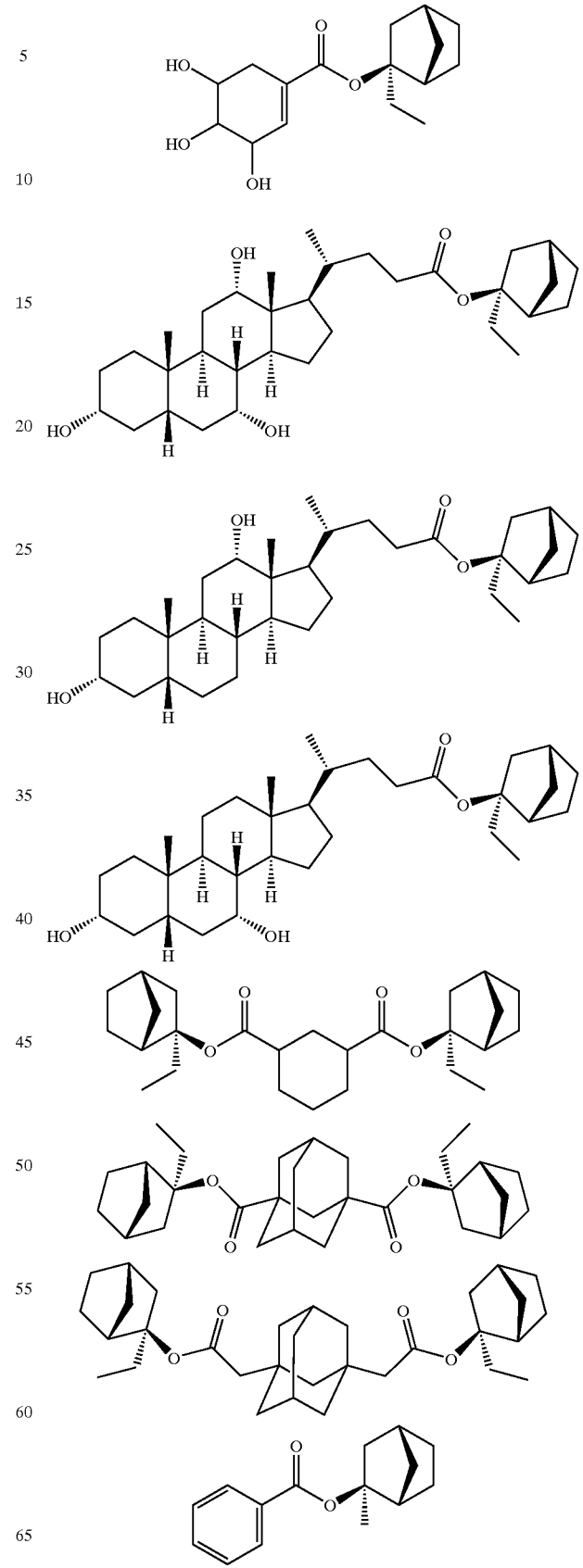

-continued
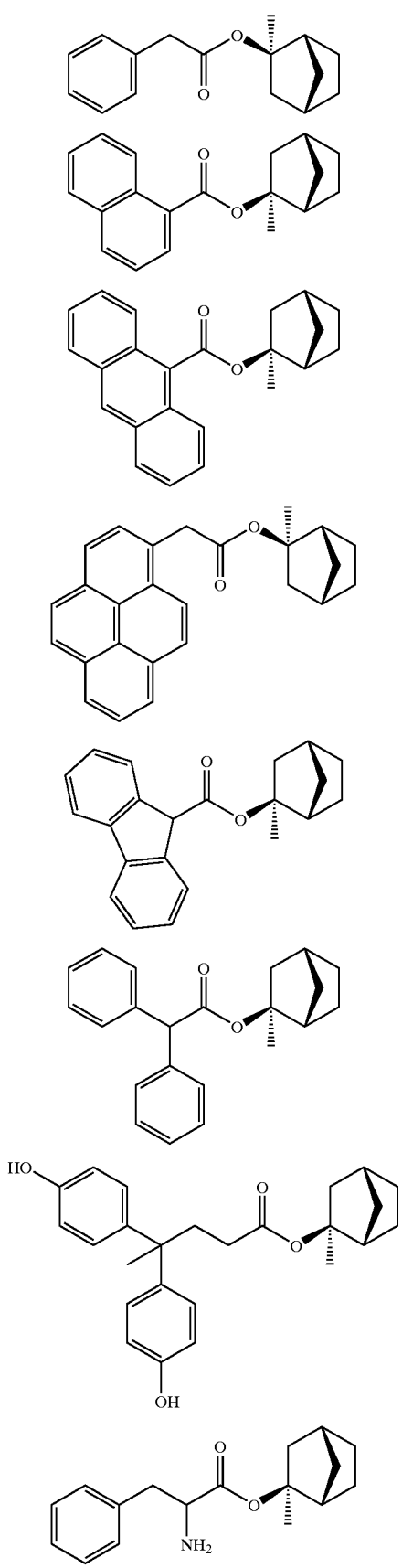
-continued
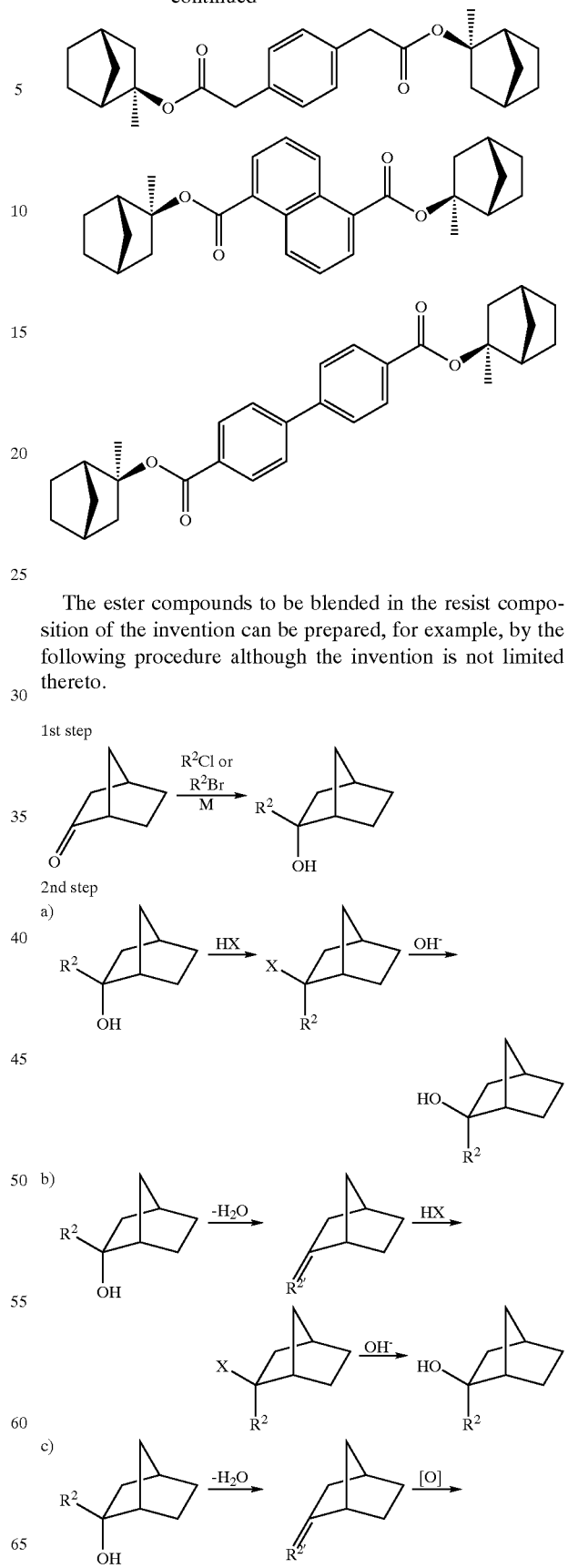
The ester compounds to be blended in the resist composition of the invention can be prepared, for example, by the following procedure although the invention is not limited thereto.

3rd step

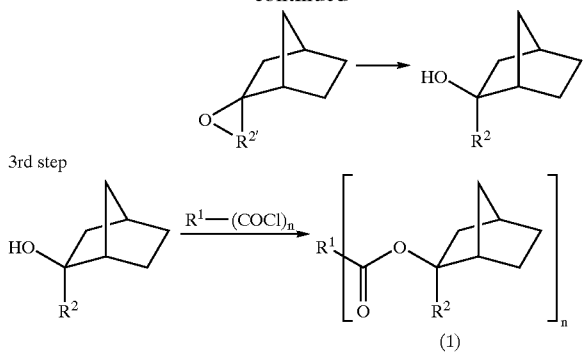

(1)

Herein, $R^1$ to $R^{12}$ and n are as defined above although $R^3$ to $R^{12}$ and n are omitted for the brevity of description. $R^{2'}$ is identical with $R^2$ except that one hydrogen atom is eliminated from the carbon at the bond position. M represents a metal, HX an acid, OH a base, [O] an oxidizing agent, and [H] a reducing agent.

The first step is to effect nucleophilic addition reaction to the carbonyl of a bicyclo[2.2.1]heptan-2-one or derivative thereof to convert it into an endo-form alcohol. Illustrative of this step are Grignard reaction and reaction using organic lithium compounds although the reaction involved in this step is not limited thereto. Reaction readily takes place under well-known conditions. Reaction is preferably carried out by mixing the reactants: a ketone compound and an alkyl halide or aryl halide with the metal M such as magnesium or lithium in a solvent such as tetrahydrofuran or diethyl ether and heating or cooling the reaction mixture if desired.

It is noted that only the endo-form alcohol yields from the first step and that the following isomerization step is essential to obtain an exo-form alcohol from which the end exo-form ester is produced.

The second step is to convert the endo-form alcohol from the first step into an exo-form alcohol. Some illustrative, non-limiting, procedures of the second step include (a) substitution reaction accompanied by stereo-inversion using acid HX, followed by alkali hydrolysis or alkali solvolysis; (b) dehydration, and addition of acid HX to the resulting olefin, followed by alkali hydrolysis or alkali solvolysis; and (c) dehydration and epoxidization of the resulting olefin, followed by reductive cleavage of epoxy. Reaction readily takes place under well-known conditions. Illustrative, non-limiting examples of the acid HX include inorganic acids such as hydrochloric acid, aqueous hydrochloric acid, hydrobromic acid, hydroiodic acid, and sulfuric acid, and organic acids such as formic acid, acetic acid, propionic acid, benzoic acid, chloroformic acid, chloroacetic acid, dichloroacetic acid, trichloroacetic acid, fluoroacetic acid, difluoroacetic acid, trifluoroacetic acid, and 3,3,3-trifluoropropionic acid. Illustrative, non-limiting examples of the base $OH^-$ include inorganic hydroxides such as sodium hydroxide, lithium hydroxide, potassium hydroxide, and barium hydroxide, inorganic carbonates such as sodium carbonate, sodium hydrogen carbonate, lithium carbonate, and potassium carbonate, and alkoxides such as sodium methoxide, sodium ethoxide, lithium methoxide, lithium ethoxide, lithium tert-butoxide, and potassium tert-butoxide, and organic bases such as diethylamine, triethylamine, tri-n-butylamine and dimethylaniline. Illustrative, non-limiting examples of the oxidizing agent [O] include peracids such as performic acid, peracetic acid, trifluoroperacetic acid, and m-chloroperbenzoic acid, and peroxides such as hydrogen peroxide, dimethyl dioxirane, and tert-butyl hydroperoxide.

It is noted that when reaction is effected using the oxidizing agent, a metal salt may be co-present as a catalyst. Illustrative, non-limiting examples of the reducing agent [H] include metal hydrides such as boran, alkylboran, dialkylboran, dialkylsilane, trialkylsilane, sodium hydride, lithium hydride, potassium hydride, and calcium hydride; complex hydride salts such as lithium boron hydride, sodium boron hydride, calcium boron hydride, lithium aluminum hydride, and sodium aluminum hydride; alkoxy complex hydride salts such as lithium trimethoxyaluminum hydride, lithium diethoxyaluminum hydride, lithium tri-tert-butoxyaluminum hydride, RED-AL, and sodium trimethoxyborohydride; and alkyl complex hydride salts such as lithium triethylborohydride, K-Selectride, and L-Selectride.

The third step is to esterify the exo-form alcohol. Reaction readily takes place under well-known conditions. Reaction is preferably carried out by successively or simultaneously adding the reactants: the exo-form alcohol, a carboxylic acid halide prepared separately, and a base (e.g., triethylamine) in a solvent such as methylene chloride and cooling the reaction mixture if desired.

It is noted that in the third step, $R^1$-$(COOH)_n$ instead of $R^1$-$(COCl)_n$ may be reacted in the presence of a dehydrating agent such as dicyclohexylcarbodiimide.

Resist Composition

As long as the ester compound of formula (1) is contained, the resist composition of the invention may be either positive working or negative working or even positive and negative working. A chemical amplification resist composition, especially chemical amplification positive resist composition is very useful.

In addition to the ester compound of formula (1), the resist composition of the invention may contain a base resin, a photoacid generator (i.e., a compound capable of generating an acid upon exposure to high energy radiation or electron beams), and an organic solvent.

Base Resin

One typical class of the base resin used herein includes those polymers comprising units of the following formula (R1) or (R2) and having a weight average molecular weight of about 1,000 to about 500,000, especially about 5,000 to about 100,000 although the base resin is not limited thereto.

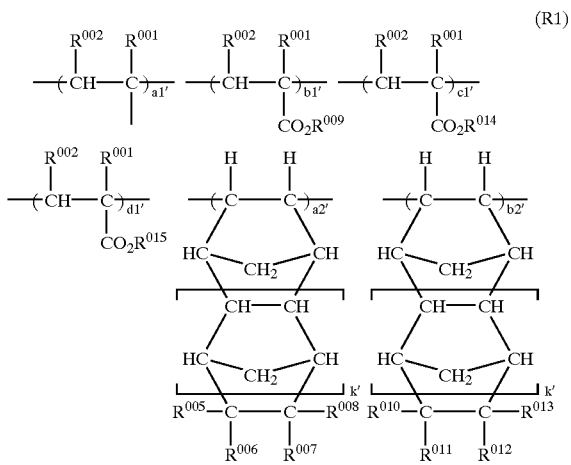

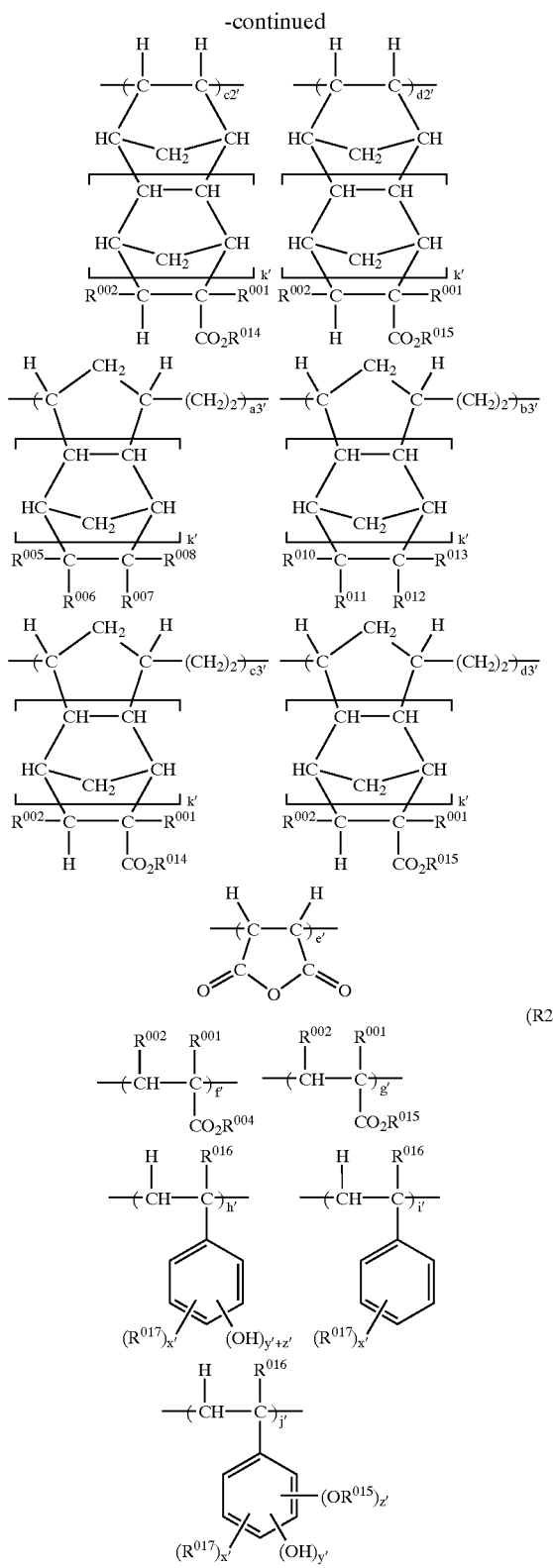

Herein, $R^{001}$ is hydrogen, methyl or $CH_2CO_2R^{003}$.

$R^{002}$ is hydrogen, methyl or $CO_2R^{003}$.

$R^{003}$ is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

$R^{004}$ is hydrogen or a monovalent hydrocarbon group of 1 to 15 carbon atoms having a carboxyl or hydroxyl group, for example, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, and hydroxyadamantyl.

At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxy-ethoxycarbonyl, 4-hydroxybutoxycarbonyl, carboxycyclopentyl-oxycarbonyl, carboxycyclohexyloxycarbonyl, carboxynorbornyl-oxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^{003}$.

Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{009}$ is a monovalent hydrocarbon group of 3 to 15 carbon atoms containing a —$CO_2$— partial structure, for example, 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. Examples of the monovalent hydrocarbon group of 2 to 15 carbon atoms containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^{003}$.

$R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently straight, branched or cyclic alkylene groups of 1 to 15 carbon atoms. Examples of the divalent hydrocarbon group of 1 to 15 carbon atoms containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group containing a —$CO_2$— partial structure, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{014}$ is a polycyclic hydrocarbon group having 7 to 15 carbon atoms or an alkyl group containing a polycyclic hydrocarbon group, for example, norbornyl, bicyclo[3.3.1]-nonyl, tricyclo[5.2.1.0$^{2,6}$]decyl, adamantyl, ethyladamantyl, butyladamantyl, norbornylmethyl, and adamantylmethyl.

$R^{015}$ is an acid labile group. $R^{016}$ is hydrogen or methyl. $R^{017}$ is a straight, branched or cyclic alkyl group of 1 to 8 carbon atoms, for example, methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl.

Letter k' is equal to 0 or 1; a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1, satisfying f'+g'+h'+i'+j'=1.

Illustrative examples of the acid labile group represented by $R^{015}$ include groups of the following formulae (A1) to (A3), tertiary alkyl groups of 4 to 20 carbon atoms, preferably 4 to 15 carbon atoms, trialkylsilyl groups whose alkyls each have 1 to 6 carbon atoms, and oxoalkyl groups of 4 to 20 carbon atoms.

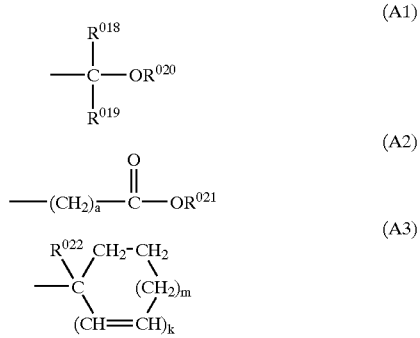

Herein, $R^{018}$ and $R^{019}$ each are hydrogen or a straight, branched or cyclic alkyl group of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl, and n-octyl. $R^{020}$ is a monovalent hydrocarbon group of 1 to 18 carbon atoms, preferably 1 to 10 carbon atoms, which may have a hetero atom such as an oxygen atom, for example, straight, branched or cyclic alkyl groups, in which some hydrogen atoms are replaced by hydroxyl, alkoxy, oxo, amino, or alkylamino groups. More illustrative of the $R^{020}$ group are the substituted alkyl groups shown below.

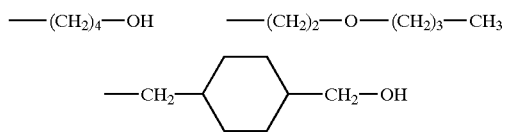

-continued

A pair of $R^{018}$ ad $R^{019}$, $R^{018}$ and $R^{020}$, or $R^{019}$ and $R^{020}$, taken together, may form a ring. $R^{018}$, $R^{019}$ and $R^{020}$ each represent straight or branched alkylene groups of 1 to 18 carbon atoms, preferably 1 to 10 carbon atoms when they form a ring.

$R^{021}$ is a tertiary alkyl group of 4 to 20 carbon atoms, preferably 4 to 15 carbon atoms, trialkylsilyl group whose alkyls each have 1 to 6 carbon atoms, oxoalkyl group of 4 to 20 carbon atoms, or group of above formula (A1). Exemplary tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl and dimethyl-tert-butylsilyl. Examples of oxoalkyl groups include 3-oxocyclohexyl, 4-methyl-2-oxooxan-4-yl, and 5-methyl-2-oxooxolan-5-yl. The letter "a" is an integer of 0 to 6.

$R^{022}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Exemplary substituted or unsubstituted aryl groups include phenyl, methylphenyl, naphthyl, anthryl, phenanthryl, and pyrenyl. The letter k is equal to 0 or 1, and m is equal to 0, 1, 2, or 3, satisfying 2k+m=2 or 3.

Of the acid labile groups of formula (A1), straight and branched groups are illustrated below.

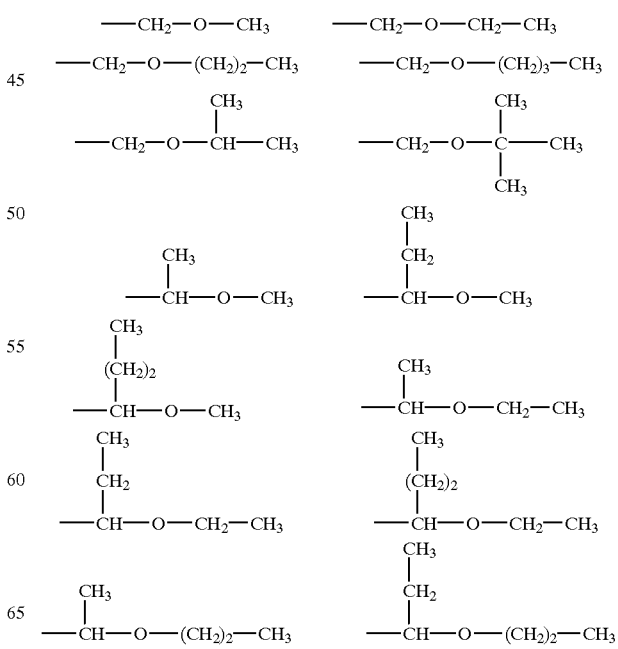

21

-continued

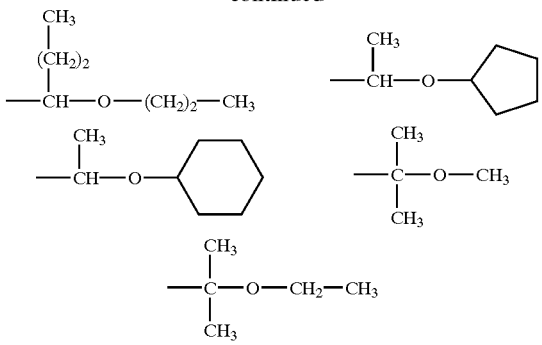

Of the acid labile groups of formula (A1), cyclic groups are illustrated below.

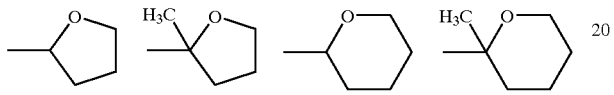

Illustrative examples of the acid labile group of formula (A2) include tert-butoxycarbonyl, tert-butoxy-carbonylmethyl, tert-amyloxycarbonyl, tert-amyloxycarbonyl-methyl, 1,1-diethylpropyloxycarbonyl, 1,1-diethylpropyloxycarbonylmethyl, 1-ethylcyclopentyloxycarbonyl, 1-ethyl-cyclopentyloxycarbonylmethyl, 1-ethyl-2-cyclopentenyloxy-carbonyl, 1-ethyl-2-cyclopentenyloxycarbonylmethyl, 1-ethoxyethoxycarbonylmethyl, 2-tetrahydropyranyloxycarbonyl-methyl, and 2-tetrahydrofuranyloxycarbonylmethyl.

Illustrative examples of the acid labile group of formula (A3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

The base resin has a weight average molecular weight of 1,000 to 500,000, preferably 3,000 to 100,000. Outside the range, the etching resistance may become extremely low and the resolution may become low because a substantial difference in rate of dissolution before and after exposure is lost.

The base resin is preferably blended in such amounts that the resist composition of the invention may contain 100 parts by weight of the base resin and 1 to 50 parts, more preferably 1 to 40 parts, and most preferably 1 to 30 parts by weight of the ester compound of formula (1). If the proportion of the base resin blended exceeds this range, the ester compound may fail to exert its effect to a full extent. If the proportion of the base resin blended is below this range, the patterned film may be thinned, leading to a decline of resolution.

The base resin is not limited to one type and a mixture of two or more base resins may be added. The use of plural base resins allows for easy adjustment of resist properties.

Photoacid Generator

The photoacid generator is a compound capable of generating an acid upon exposure to high energy radiation or electron beams and includes the following:

22

(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.

(i) Onium Salts of Formula (P1a-1), (P1a-2) or (P1b):

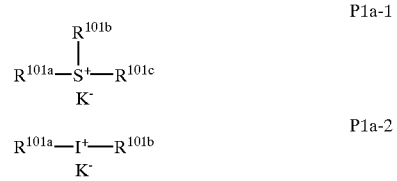

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101C}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoro-ethanesulfonate, and nonafluorobutanesulfonate, arylsulfonate ions such as tosylate, benzenesulfonate, 4-fluorobenzenesulfonate, and 1,2,3,4,5-pentafluorobenzene-sulfonate, and alkylsulfonate ions such as mesylate and butanesulfonate.

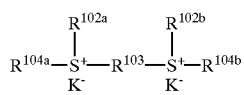

P1b

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclo-pentyl, 2-oxocyclohexyl, and 2-oxocycloheptyl. Illustrative examples of the counter ion represented by $K^-$ are the same as exemplified for formulae (Pla-1) and (Pla-2).

(ii) Diazomethane Derivatives of Formula (P2)

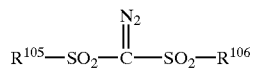

P2

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

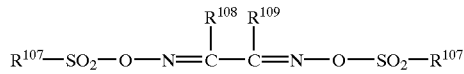

P3

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

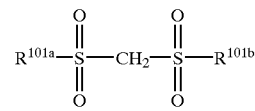

P4

Herein, $R^{101a}$ and $R^{101b}$ are as defined above.

(v) Sulfonic Acid Esters of N-hydroxyimide Compounds of Formula (P5)

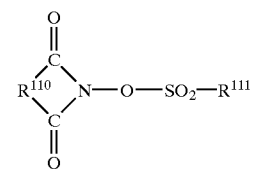

P5

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:

onium salts such as diphenyliodonium trifluoromethanesulfonate, (p-tert-butoxyphenyl)phenyliodonium trifluoromethanesulfonate, diphenyliodonium p-toluene-sulfonate, (p-tert-butoxyphenyl)phenyliodonium p-toluene-sulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis-[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)-diazomethane, bis(p-toluenesulfonyl)diazomethane, bis(xylenesulfonyl)diazomethane, bis(cyclohexylsulfonyl)-diazomethane, bis(cyclopentylsulfonyl)diazomethane, bis(n-butylsulfonyl)diazomethane, bis(isobutylsulfonyl)-diazomethane, bis(sec-butylsulfonyl)diazomethane, bis(n-propylsulfonyl)diazomethane, bis(isopropylsulfonyl)-diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-o-(p-toluene-sulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-o-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluoro-octanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, and bis-o-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethane-sulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl) sulfonium trifluoromethanesulfonate, triphenylsulfonium p-toluenesulfonate, (p-tert-butoxyphenyl) diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)-diazomethane, bis(n-butylsulfonyl)diazomethane, bis(isobutylsulfonyl)diazomethane, bis(sec-butylsulfonyl)-diazomethane, bis(n-propylsulfonyl)diazomethane, bis(isopropylsulfonyl)diazomethane, and bis(tert-butylsulfonyl)diazomethane; glyoxime derivatives such as bis-o-(p-toluenesulfonyl)-α-dimethylglyoxime and bis-o-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would lower the rate of alkali dissolution to reduce the resolution of resist compositions and also lower the heat resistance because of the excessive presence of lower molecular weight components.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator serving as one of the resist components is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

Dissolution Regulator

In addition to the ester compound of formula (1), another dissolution regulator may be added to the resist composition. A variety of dissolution regulators are useful although typical dissolution regulators are compounds having an average molecular weight within a range of 100 to 1,000, and preferably 150 to 800, and bearing on the molecule at least two phenolic hydroxyl groups or at least one carboxyl group, in which 0 to 100 mol % and preferably 0 to 80 mol % of the phenolic hydroxyl groups or carboxyl groups are protected with acid labile groups.

Preferable examples of such compounds having two or more phenolic hydroxyl groups or compounds having one or more carboxyl groups include those of formulas (D1) to (D14) below.

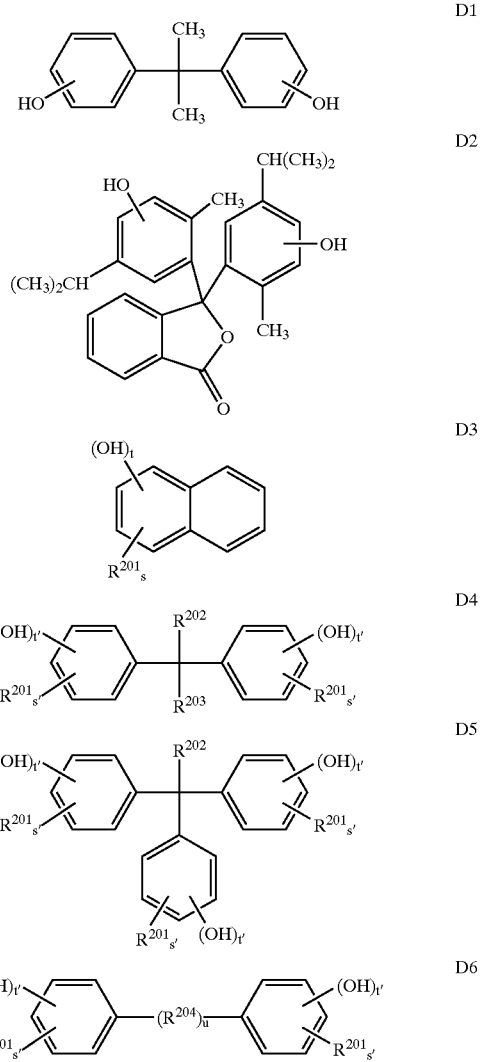

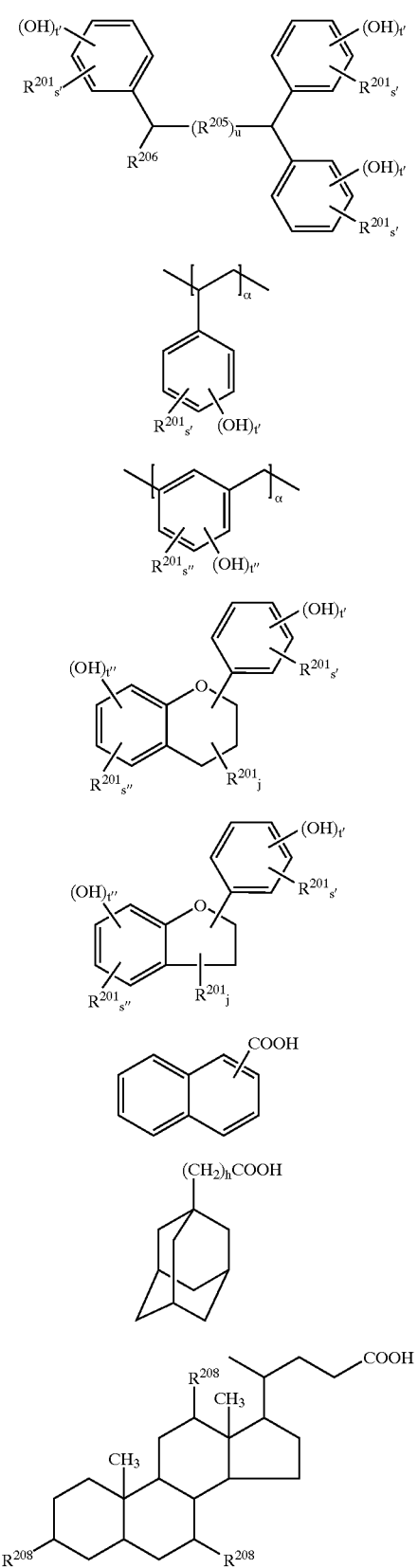

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or $-(R^{207})_h-COOH$; $R^{204}$ is $-(CH_2)_i-$ (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and α is a number such that the molecular weight of the compounds of formula (D8) or (D9) is from 100 to 1,000.

In the above formulas, suitable examples of $R^{201}$ and $R^{202}$ include hydrogen, methyl, ethyl, butyl, propyl, ethynyl, and cyclohexyl; suitable examples of $R^{203}$ include the same groups as for $R^{201}$ and $R^{202}$, as well as $-COOH$ and $-CH_2COOH$; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, butyl, propyl, ethynyl, cyclohexyl, and hydroxyl-substituted phenyl or naphthyl.

Exemplary acid labile groups on the dissolution regulator include groups of the following general formulae (A1) to (A3), tertiary alkyl groups of 4 to 20 carbon atoms, trialkylsilyl groups in which each of the alkyls has 1 to 6 carbon atoms, and oxoalkyl groups of 4 to 20 carbon atoms.

$$\begin{array}{c} R^{018} \\ | \\ -C-OR^{020} \\ | \\ R^{019} \end{array} \quad (A1)$$

$$-(CH_2)_a-\overset{O}{\overset{\|}{C}}-OR^{021} \quad (A2)$$

$$\begin{array}{c} R^{022} \;\; CH_2\text{-}CH_2 \\ \diagdown \;\; \diagup \\ -C \;\;\;\; (CH_2)_m \\ \diagup \;\; \diagdown \\ (CH=CH)_k \end{array} \quad (A3)$$

Herein, $R^{018}$ to $R^{022}$, a, k and m are as defined above.

The other dissolution regulator may be formulated in an amount of 0 to 50 parts, preferably 5 to 50 parts, and more preferably 10 to 30 parts, per 100 parts of the base resin, and may be used singly or as a mixture of two or more thereof. Less than 5 parts of the dissolution regulator may fail to yield an improved resolution, whereas the use of more than 50 parts would lead to thinning of the patterned film, and thus a decline in resolution.

The other dissolution regulator can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropyl-amine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]-piperazine, piperidine ethanol, 1-(2-hydroxyethyl)-pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)-isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (B1) and (B2) may also be included.

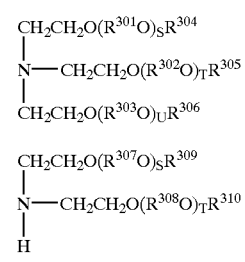

In the formulas, $R^{301}$, $R^{302}$, $R^{303}$, $R^{307}$ and $R^{308}$ are independently straight, branched or cyclic alkylenes of 1 to 20 carbon atoms; $R^{304}$, $R^{305}$, $R^{306}$, $R^{309}$ and $R^{310}$ are hydrogen, alkyls of 1 to 20 carbon atoms, or amino; $R^{304}$ and $R^{305}$, $R^{304}$ and $R^{306}$, $R^{305}$ and $R^{307}$, $R^{304}$ with $R^{305}$ and $R^{306}$ and $R^{309}$ and $R^{310}$ may bond together to form rings; and S, T and U are each integers from 0 to 20, with the proviso that hydrogen is excluded from $R^{304}$, $R^{305}$, $R^{306}$, $R^{309}$ and $R^{310}$ when S, T and U are equal to 0.

The alkylene groups represented by $R^{301}$, $R^{302}$, $R^{303}$, $R^{307}$ and $R^{308}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{304}$, $R^{305}$, $R^{306}$, $R^{309}$ and $R^{310}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{304}$ and $R^{305}$, $R^{304}$ and $R^{306}$, $R^{305}$ and $R^{306}$, $R^{304}$ with $R^{305}$ and $R^{306}$, and $R^{309}$ and $R^{310}$ form rings, the rings preferably have 1 to 20 carbon atoms, more preferably 1 to 8 carbon atoms, and most preferably 1 to 6 carbon atoms, and may have branching alkyl groups of 1 to 6 carbon atoms, and especially 1 to 4 carbon atoms.

S, T, and U are each integers from 0 to 20, preferably from 1 to 10, and more preferably from 1 to 8.

Illustrative examples of the compounds of formulas (B1) and (B2) include tris{2-(methoxymethoxy)ethyl}amine, tris{2-(methoxyethoxy)ethyl}amine, tris[2-{(2-methoxyethoxy)methoxy}ethyl]amine, tris{2-(2-methoxyethoxy)-ethyl}amine, tris{2-(1-methoxyethoxy)ethyl}amine, tris{2-(1-ethoxyethoxy)ethyl}amine, tris{2-(1-ethoxypropoxy)-ethyl}amine, tris[2-{(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, and 1-aza-18-crown-6. Especially preferred basic compounds are tertiary amines, aniline derivatives, pyrrolidine derivatives, pyridine derivatives, quinoline derivatives, amino acid derivatives, hydroxyl group-bearing nitrogenous compounds, hydroxyphenyl group-bearing nitrogenous compounds, alcoholic nitrogenous compounds, amide derivatives, imide derivatives, tris{2-(methoxymethoxy)ethyl}amine, tris{2-(2-methoxyethoxy)-ethyl}amine, tris[2-{(2-methoxyethoxy)methyl}ethyl]amine, and 1-aza-15-crown-5.

The basic compound is preferably formulated in an amount of 0.001 to 10 parts, and especially 0.01 to 1 part, per part of the photoacid generator. Less than 0.001 part of the basic compound fails to achieve the desired effects thereof, while the use of more than 10 parts would result in too low a sensitivity and resolution.

Other Components

In the resist composition, a compound bearing a $\equiv$C—COOH group in a molecule may be blended. Exemplary, non-limiting compounds bearing a $\equiv$C—COOH group include one or more compounds selected from Groups I and II below. Including this compound improves the PED stability of the resist and ameliorates edge roughness on nitride film substrates.

Group I:

Compounds in which some or all of the hydrogen atoms on the phenolic hydroxyl groups of the compounds of general formulas (A1) to (A10) below have been replaced with —$R^{401}$—COOH (wherein $R^{401}$ is a straight or branched alkyl of 1 to 10 carbon atoms), and in which the molar ratio C/(C+D) of phenolic hydroxyl groups (C) to $\equiv$C—COOH groups (D) in the molecule is from 0.1 to 1.0.

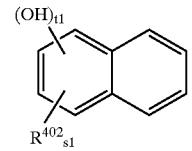

A1

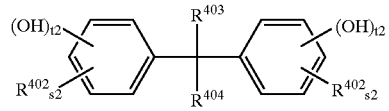

A2

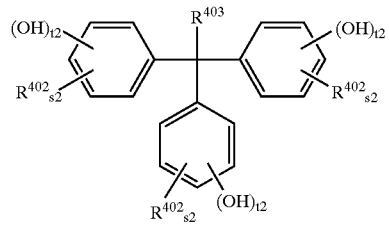

A3

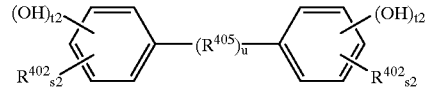

A4

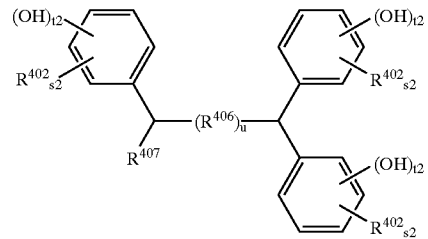

A5

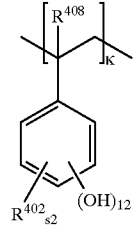

A6

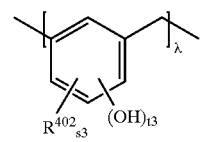

A7

-continued

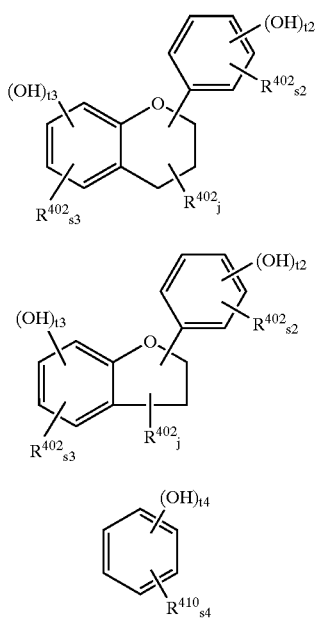

A8

A9

A10

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a —$(R^{409})_h$—COOR' group (R' being hydrogen or —$R^{409}$—COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$— COOH group; $R^{411}$ is a straight or branched alkylene of 1 to 10 carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:
Compounds of general formulas (A11) to (A15) below.

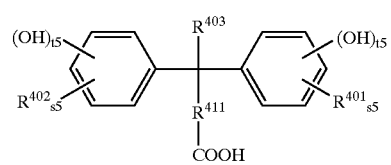

A11

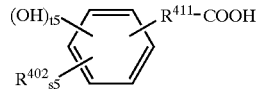

A12

-continued

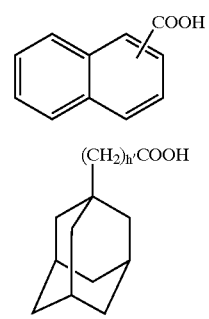

A13

A14

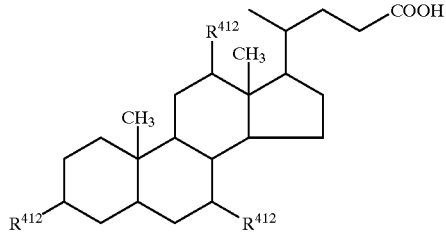

A15

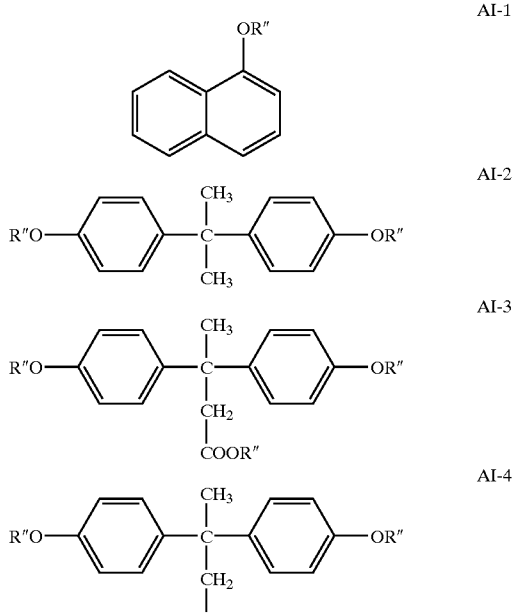

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

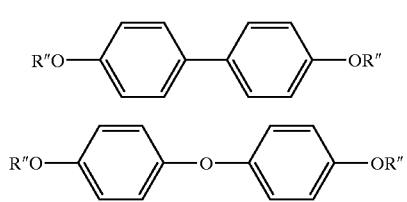

AI-1

AI-2

AI-3

AI-4

AI-5

AI-6

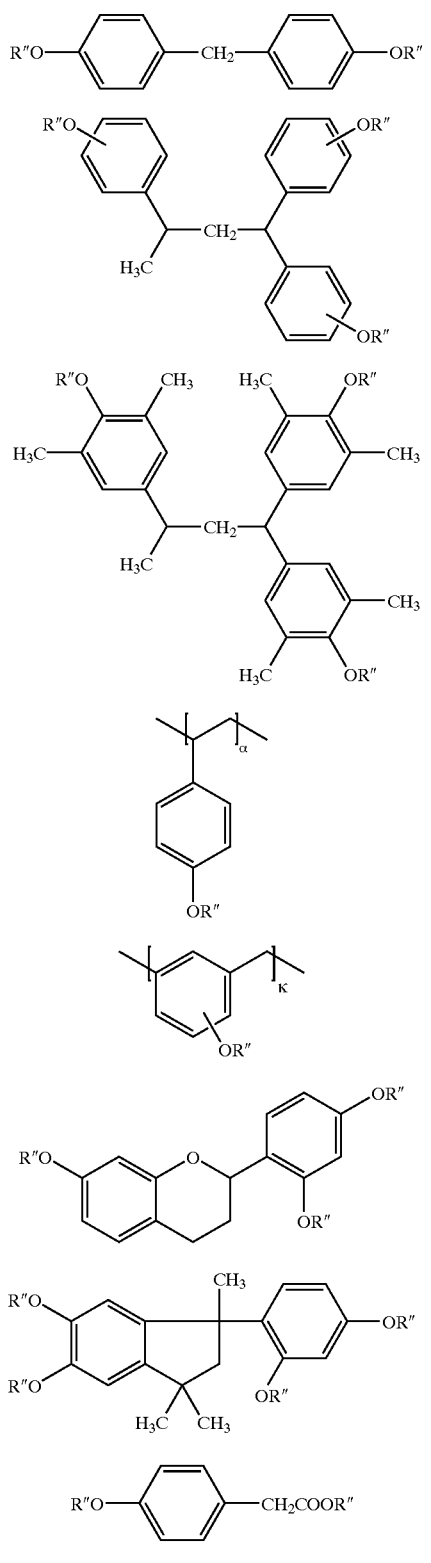
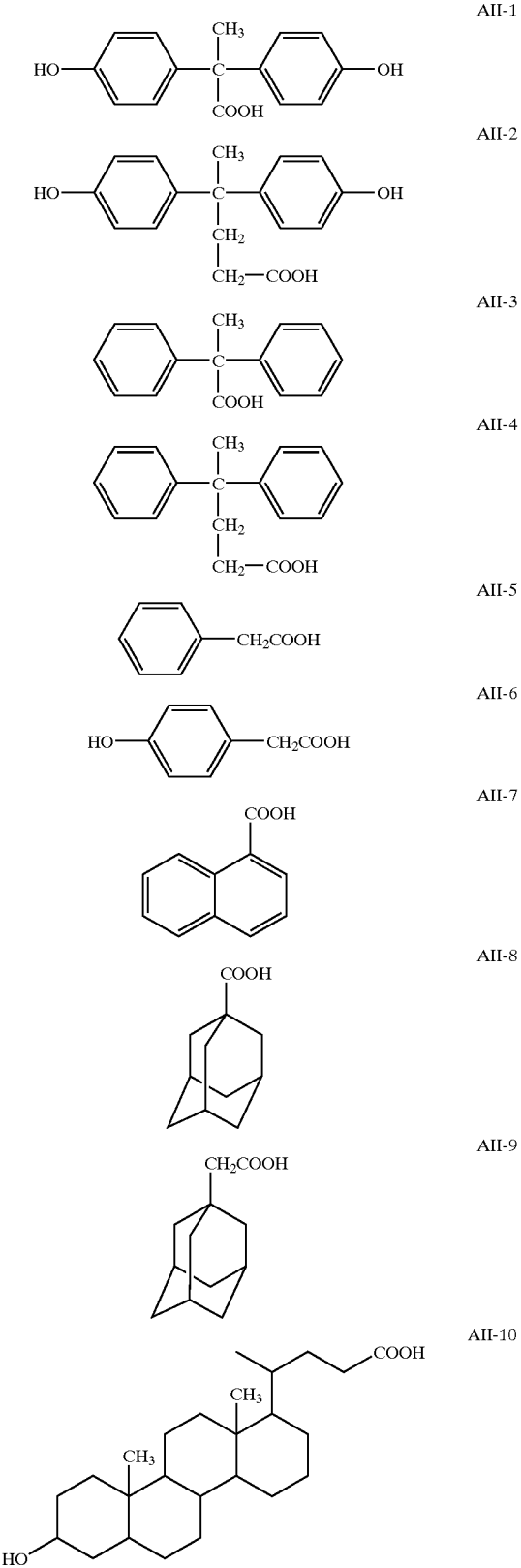
In the above formulas, R″ is hydrogen or a CH₂COOH group such that the CH₂COOH group accounts for 10 to 100 mol % of R″ in each compound, α and κ are as defined above.
The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (S1) or (S2) below.

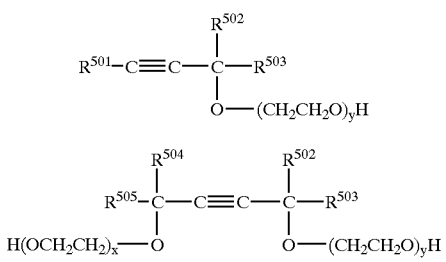

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include, as an optional ingredient, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M K.K., Surflon S-141 and S-145 from Asahi Glass K.K., Unidine DS-401, DS-403 and DS-451 from Daikin Industry K.K., Megaface F-8151 from Dai-Nippon Ink & Chemicals K.K., and X-70-092 and X-70-093 from Shin-Etsu Chemical Co., Ltd. Preferred surfactants are Florade FC-430 from Sumitomo 3M K.K. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 5 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 193 to 248 nm, an excimer laser, x-rays, or an electron beam. The desired pattern may not be obtainable outside the upper and lower limits of the above range.

The resist composition comprising the ester compound lends itself to micropatterning with electron beams or deep-UV rays since it is sensitive to high-energy radiation and has excellent sensitivity, resolution, etching resistance, and shelf stability. Especially because of the minimized absorption at the exposure wavelength of an ArF or KrF excimer laser, a finely defined pattern having sidewalls perpendicular to the substrate can easily be formed.

EXAMPLE

Examples of the invention are given below by way of illustration and not by way of limitation.

Ester compounds to be blended in the resist compositions of the invention are synthesized by the following procedure.

Synthetic Example 1

Synthesis of DRR1

In 600 ml of tetrahydrofuran was dissolved 148.5 g of ethyl bromide. Below 60° C., this reaction mixture was added dropwise to 32.4 g of metallic magnesium over one hour. After agitation was continued for 2 hours at room temperature, 110.2 g of bicyclo[2.2.1]heptan-2-one was added dropwise over 45 minutes to the reaction mixture which was kept below 65° C. After agitation was continued for one hour at room temperature, the reaction solution was worked up in a conventional manner. The resulting oily substance was distilled in vacuum, collecting 126.9 g of 2-ethylbicyclo[2.2.1]heptan-2-ol in endo-form. The yield was 90.5%.

In 600 ml of benzene was dissolved 125.0 g of 2-ethylbicyclo[2.2.1]heptan-2-ol in endo-form. To the solution was added 8.5 g of p-toluenesulfonic acid monohydrate. This reaction mixture was heated, agitated under reflux for 6 hours while removing water, and subjected to conventional post-treatment. The resulting oily substance was purified by silica gel column chromatography, obtaining 85.9 g of 2-ethylidenebicyclo[2.2.1]heptane. The yield was 78.8%.

In 500 ml of methylene chloride was dissolved 84.0 g of 2-ethylidenebicyclo[2.2.1]heptane. To this solution was added 219.0 g of 65% m-chloroperbenzoic acid. This reaction mixture was agitated for 12 hours at 4° C. and subjected to conventional post-treatment, obtaining an oily substance. This was used in the subsequent reaction without purification.

The oily substance obtained in the above step was dissolved in 200 ml of diethyl ether. With stirring, this solution was added dropwise to a suspension of 26.2 g of aluminum lithium hydride in 200 ml of diethyl ether under ice cooling. The reaction mixture was agitated for a further 2 hours at room temperature and subjected to conventional post-treatment. The resulting oily substance was distilled in vacuum, obtaining 87.0 g of 2-ethylbicyclo[2.2.1]heptan-2-ol in exo-form. The yield was 90.3%.

In 200 ml of methylene chloride was dissolved 35.0 g of 2-ethylbicyclo[2.2.1]heptan-2-ol in exo-form. With stirring, 47.0 g of norbornane-2-carboxylic acid chloride and then 54.4 g of triethylamine were added dropwise to the solution under ice cooling. The reaction mixture was agitated for a further 12 hours at room temperature and subjected to conventional post-treatment. The resulting oily substance was distilled in vacuum, collecting 54.9 g of 2-ethylbicyclo[2.2.1]heptan-2-yl norbornane-2-carboxylate in exo-form, designated DRR1. The yield was 83.3%.

$^{1}$H-NMR (270 MHz): d=0.80 (3H, t), 1.00–2.05 (17H, m), 2.05–2.65 (6H, m); IR: n=2962, 2871, 1724, 1187, 1168, 1132, 1114 cm$^{-1}$.

Synthetic Example 2

Synthesis of DRR2

As above, 2-ethylbicyclo[2.2.1]heptan-2-yl 1-adamantanecarboxylate in exo-form, designated DRR2, was synthesized from bicyclo[2.2.2]heptan-2-one.

$^{1}$H-NMR (270 MHz): d=0.78 (3H, t), 1.05 (1H, m), 1.18 (1H, m), 1.25–1.60 (4H, m), 1.60–2.05 (18H, m), 2.10–2.30 (2H, m), 2.54 (1H, m); IR (KBr): n=2964, 2933, 2906, 2850, 1716, 1452, 1325, 1267, 1223, 1221, 1174, 1103, 1078 cm$^{-1}$.

Synthetic Example 3

Synthesis of DRR3

As above, 8-methyltricyclo[5.2.1.0$^{2.6}$]decan-8-yl 1-adamantanecarboxylate in exo-form, designated DRR3, was synthesized from tricyclo[5.2.1.1.0$^{2.6}$]decan-8-one.

$^{1}$H-NMR (270 MHz): d=0.79 (3H, d), 0.85–1.45 (6H, m), 1.60–2.05 (23H, m), 2.16 (1H, dq), 2.34 (1H, m); IR (KBr): n=2935, 2904, 2852, 1716, 1452, 1326, 1267, 1236, 1234, 1211, 1161, 1103, 1076 cm$^{-1}$.

Synthetic Example 4

Synthesis of DRR4

As above, 2-ethylbicyclo[2.2.1]heptan-2-yl cholate in exo-form, designated DRR4, was synthesized from bicyclo[2.2.1]heptan-2-one.

$^{1}$H-NMR (270 MHz): d=0.66 (3H, s), 0.80 (3H, t), 0.87 (3H, s), 0.90–2.05 (35H, m), 2.05–2.35 (6H, m), 2.51 (1H, m), 3.42 (1H, m), 3.81 (1H, m), 3.95 (1H, m); IR (KBr): n=3435, 2964, 2937, 2870, 1726, 1464, 1377, 1329, 1311, 1267, 1223, 1194, 1171, 1078, 1045 cm$^{-1}$.

Synthetic Example 5

Synthesis of DRR5

As above, 2-ethylbicyclo[2.2.1]heptan-2-yl triformylcholate in exo-form, designated DRR5, was synthesized from bicyclo[2.2.1]heptan-2-one.

$^{1}$H-NMR (270 MHz): d=0.74 (3H, s), 0.81 (3H, t), 0.93 (3H, s), 1.00–2.30 (38H, m), 2.50 (1H, m), 4.70 (1H, m), 5.06 (1H, m), 5.25 (1H, m), 8.01 (1H, s), 8.09 (1H, s), 8.14 (1H, s); IR (KBr): n=2964, 2875, 1720, 1465, 1378, 1250, 1248, 1182 cm$^{-1}$.

Synthetic Example 6

Synthesis of DRR6

As above, 2-ethylbicyclo[2.2.1]heptan-2-yl 1-adamantaneacetate in exo-form, designated DRR6, was synthesized from bicyclo[2.2.1]heptan-2-one.

$^{1}$H-NMR (270 MHz): d=0.82 (3H, t), 1.05 (1H, m), 1.20 (1H, m), 1.30–1.80 (18H, m), 1.90–2.05 (6H, m), 2.21 (1H, m), 2.28 (1H, dq), 2.50 (1H, m); IR (KBr): n=2964, 2902, 2848, 1722, 1454, 1328, 1261, 1197, 1174, 1130, 1101 cm$^{-1}$.

Synthetic Examples 7–14

Synthesis of DRR7–14

DRR7 to DRR14 were synthesized by the same procedure as above.

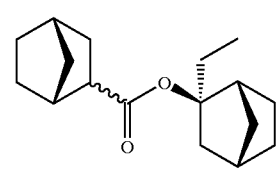

DRR 1

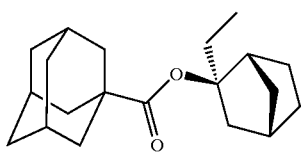

DRR 2

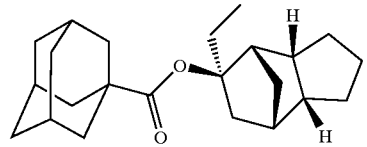

DRR 3

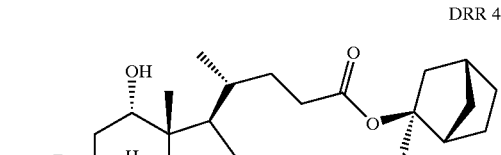

DRR 4

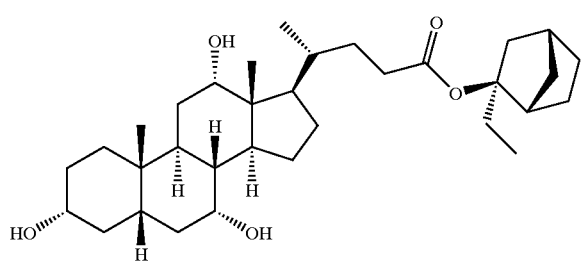

DRR 5

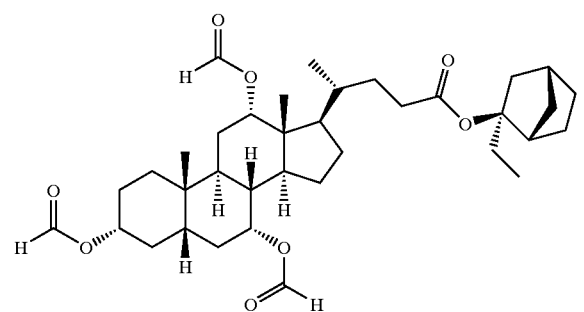

DRR 6
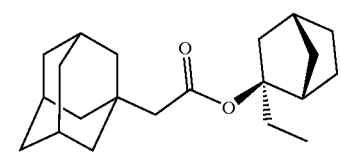

DRR 7
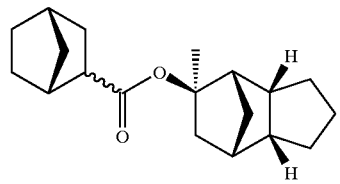

DRR 8
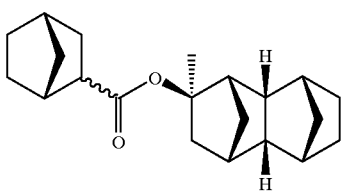

DRR 9
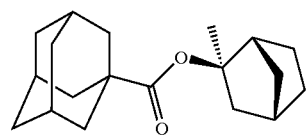

DRR 10
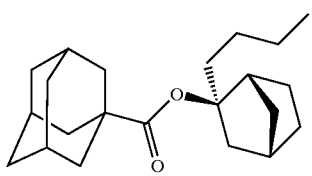

DRR 11
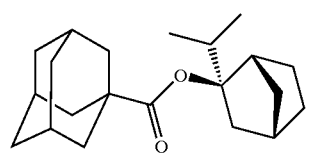

DRR 12
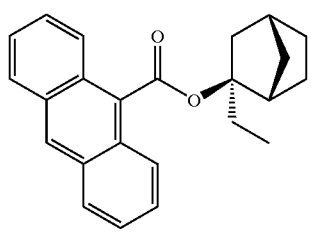

DRR 13
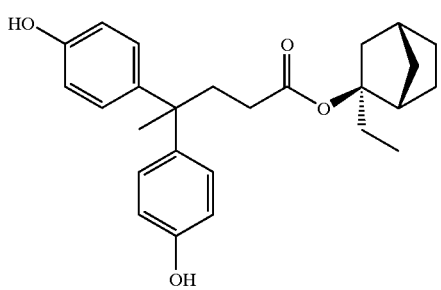

DRR 14
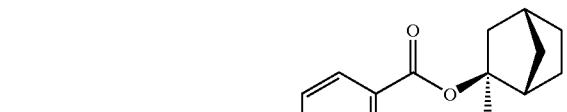

Examples and Comparative Examples

The ester compounds DRR1 to DRR14 obtained in the Synthetic Examples were formulated into resist materials, whose performance was examined. For comparison purposes, a similar resist material without the ester compound was formulated and examined.

The components used herein were a polymer (Polymer 1 to Polymer 12), a photoacid generator (PAG1 to PAG8), a dissolution regulator (DRR15 to DRR18), a compound having a ≡C—COOH group in the molecule (ACC1 and ACC2), and a solvent, which were selected in the combination shown in Tables 1 to 5. The solvent contained 0.05% by weight of surfactant Florade FC-430 (Sumitomo 3M).

The solvents and basic compounds used are as follows.

PGMEA: propylene glycol methyl ether acetate
PG/EL: a mixture of 70% PGMEA and 30% ethyl lactate
TBA: tributylamine
TEA: triethanolamine
TMMEA: trismethoxymethoxyethylamine
TMEMEA: trismethoxyethoxymethoxyethylamine (Polymer 1)
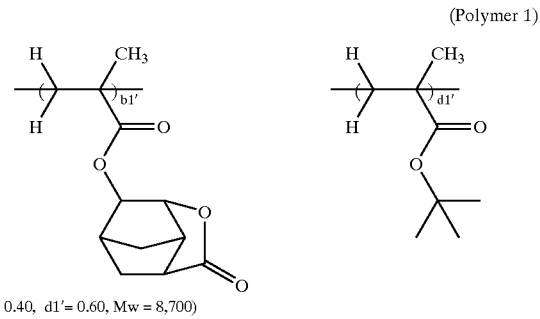
($b1' = 0.40$, $d1' = 0.60$, Mw = 8,700)

(Polymer 2)
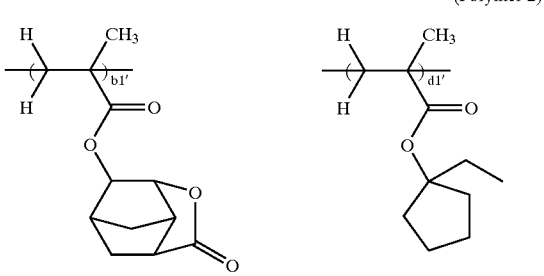
($b1' = 0.30$, $d1' = 0.70$, Mw = 9,700)

(Polymer 3)
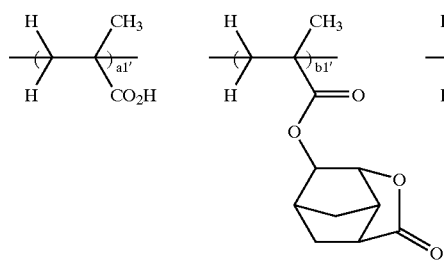
(a1' = 0.10, b1' = 0.25, d1' = 0.65, Mw = 7,800)
(Polymer 4)
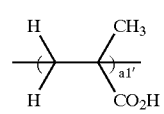
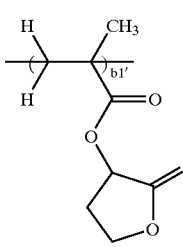
(a1' = 0.10, b1' = 0.20, c1' = 0.30, d1' = 0.40, Mw = 9,300)
(Polymer 5)
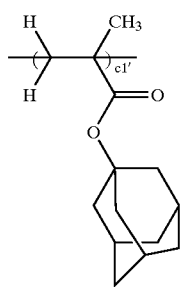
(d2' = 0.50, e' = 0.50, Mw = 11,000
(Polymer 6)
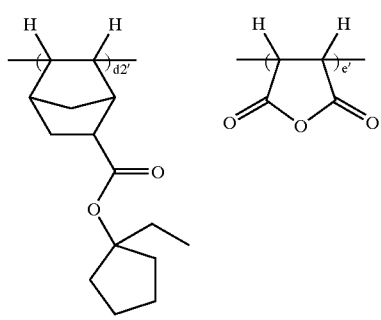
(d2' = 0.50, e' = 0.50, Mw = 12,500)
(Polymer 7)
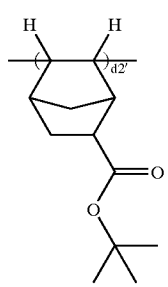
(a2' = 0.10, b2' = 0.30, d2' = 0.60, Mw = 27,600)
(Polymer 8)
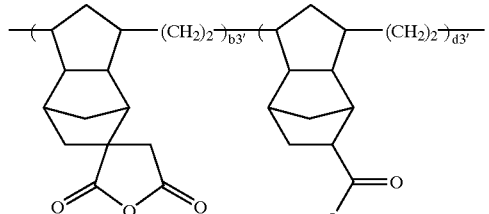
(b3' = 0.40, d3' = 0.60, Mw = 38,400)
(Polymer 9)
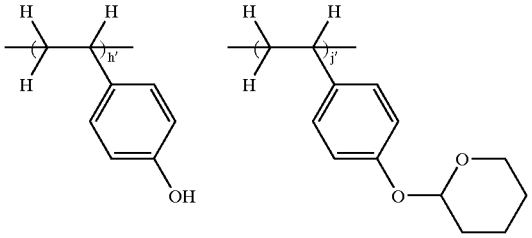
(h' = 0.65, j' = 0.35, Mw = 12,700)
(Polymer 10)
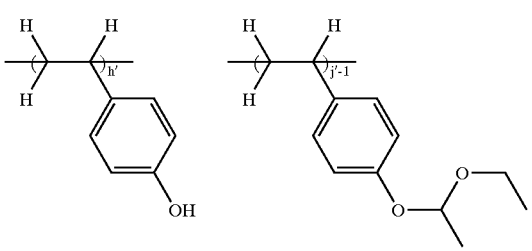
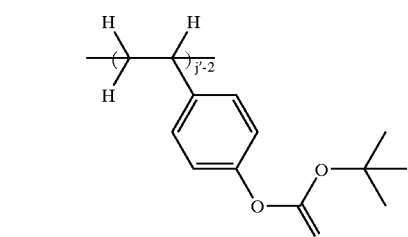
(h' = 0.70, j'-1 = 0.15, j'-2 = 0.15, Mw = 12,400)

(Polymer 11)
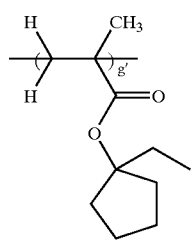
(g' = 0.30, h' = 0.70, Mw = 11,800)
(Polymer 12)
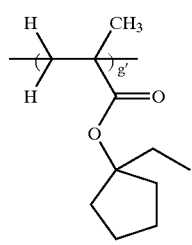
(g' = 0.25, h' = 0.60, i' = 0.15, Mw = 11,300)
(PAG 1)
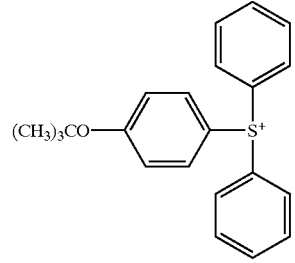 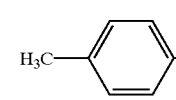
(PAG 2)
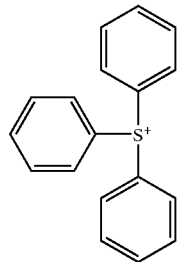
(PAG 3)
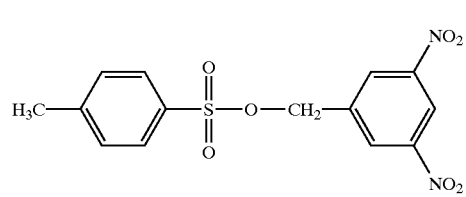
(PAG 4)
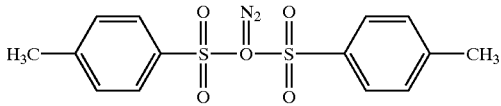
(PAG 5)
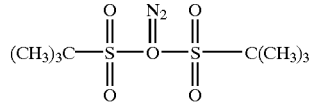
(PAG 6)
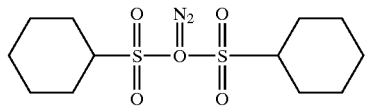
(PAG 7)
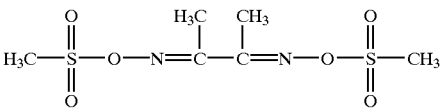
(PAG 8)
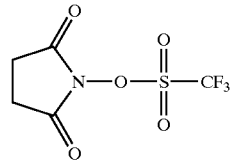
(DRR 15)
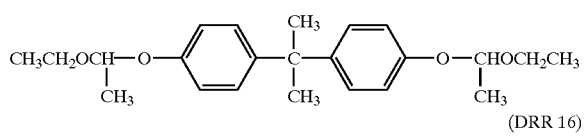
(DRR 16)
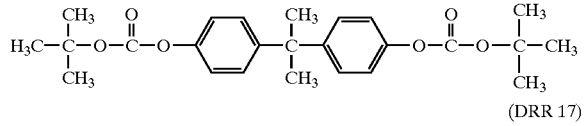
(DRR 17)
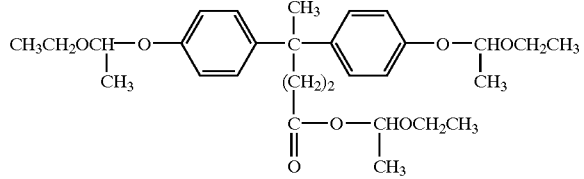
(DRR 18)
(ACC 1)
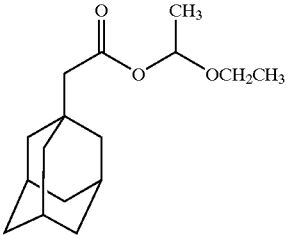

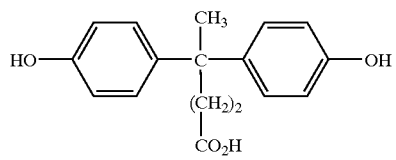

(ACC 2)

Examples I-1 to I-35

Resist materials were formulated in accordance with the formulation shown in Tables 1 and 2. These materials were each filtered through a 0.2-μm Teflon filter, thereby giving resist solutions. These resist solutions were spin-coated onto silicon wafers, then baked at 110° C. for 90 seconds on a hot plate to give resist films having a thickness of 0.5 μm. The resist films were exposed using an ArF excimer laser stepper (Nikon Corporation; NA 0.55), then baked (PEB) at 110° C. for 90 seconds, and developed with a solution of 2.38% tetramethylammonium hydroxide in water, thereby giving positive patterns.

The resulting resist patterns were evaluated as described below. First, the sensitivity (mJ/cm$^2$) was determined as the dose which provides a 1:1 resolution at the top and bottom of a 0.25 μm line-and-space pattern. The resolution of the resist under evaluation was defined as the minimum line width (μm) of the lines and spaces that separated at this dose. The shape of the resolved resist pattern was examined under a scanning electron microscope.

The composition and test results of the resist materials are shown in Tables 1 and 2.

TABLE 1

| Example | Resin | Photoacid generator | Dissolution regulator | Basic compound | Solvent | Sensitivity | Resolution | shape |
|---------|-------|--------------------|-----------------------|----------------|---------|-------------|------------|-------|
| I-1 | Polymer 1 (64) | PAG 1 (2) | DRR 1 (16) | TBA (0.125) | PGMEA (480) | 31.2 | 0.18 | rectangular |
| I-2 | Polymer 1 (64) | PAG 1 (2) | DRR 2 (16) | TBA (0.125) | PGMEA (480) | 31.8 | 0.18 | rectangular |
| I-3 | Polymer 1 (64) | PAG 1 (2) | DRR 3 (16) | TBA (0.125) | PGMEA (480) | 32.1 | 0.18 | rectangular |
| I-4 | Polymer 1 (64) | PAG 1 (2) | DRR 4 (16) | TBA (0.125) | PGMEA (480) | 34.5 | 0.18 | rectangular |
| I-5 | Polymer 1 (64) | PAG 1 (2) | DRR 5 (16) | TBA (0.125) | PGMEA (480) | 32.4 | 0.18 | rectangular |
| I-6 | Polymer 1 (64) | PAG 1 (2) | DRR 6 (16) | TBA (0.125) | PGMEA (480) | 32.4 | 0.18 | rectangular |
| I-7 | Polymer 1 (64) | PAG 1 (2) | DRR 7 (16) | TBA (0.125) | PGMEA (480) | 32.1 | 0.18 | rectangular |
| I-8 | Polymer 1 (64) | PAG 1 (2) | DRR 8 (16) | TBA (0.125) | PGMEA (480) | 31.8 | 0.18 | rectangular |
| I-9 | Polymer 1 (64) | PAG 1 (2) | DRR 9 (16) | TBA (0.125) | PGMEA (480) | 33.0 | 0.18 | rectangular |
| I-10 | Polymer 1 (64) | PAG 1 (2) | DRR 10 (16) | TBA (0.125) | PGMEA (480) | 32.4 | 0.18 | rectangular |
| I-11 | Polymer 1 (64) | PAG 1 (2) | DRR 11 (16) | TBA (0.125) | PGMEA (480) | 30.6 | 0.18 | rectangular |
| I-12 | Polymer 3 (64) | PAG 1 (2) | DRR 2 (16) | TBA (0.125) | PG/EL (480) | 30.6 | 0.18 | rectangular |
| I-13 | Polymer 3 (64) | PAG 2 (2) | DRR 2 (16) | TBA (0.125) | PG/EL (480) | 17.1 | 0.18 | rectangular |
| I-14 | Polymer 3 (64) | PAG 3 (2) | DRR 2 (16) | TBA (0.125) | PG/EL (480) | 29.7 | 0.18 | rectangular |
| I-15 | Polymer 3 (64) | PAG 4 (2) | DRR 2 (16) | TBA (0.125) | PG/EL (480) | 29.3 | 0.18 | rectangular |
| I-16 | Polymer 3 (64) | PAG 5 (2) | DRR 2 (16) | TBA (0.125) | PG/EL (480) | 27.9 | 0.18 | rectangular |
| I-17 | Polymer 3 (64) | PAG 6 (2) | DRR 2 (16) | TBA (0.125) | PG/EL (480) | 28.4 | 0.18 | rectangular |
| I-18 | Polymer 3 (64) | PAG 7 (2) | DRR 2 (16) | TBA (0.125) | PG/EL (480) | 18.0 | 0.18 | rectangular |
| I-19 | Polymer 3 (64) | PAG 8 (2) | DRR 2 (16) | TBA (0.125) | PG/EL (480) | 15.8 | 0.18 | rectangular |
| I-20 | Polymer 2 (32) Polymer 4 (32) | PAG 2 (2) | DRR 7 (16) | TBA (0.125) | PGMEA (480) | 12.0 | 0.18 | rectangular |

TABLE 2

| Example | Resin | Photoacid generator | Dissolution regulator | Basic compound | Solvent | Sensitivity | Resolution | shape |
|---|---|---|---|---|---|---|---|---|
| I-21 | Polymer 2 (32) Polymer 4 (32) | PAG 2 (2) | DRR 7 (16) | TEA (0.125) | PGMEA (480) | 11.4 | 0.15 | rectangular |
| I-22 | Polymer 2 (32) Polymer 4 (32) | PAG 2 (2) | DRR 7 (16) | TMMEA (0.125) | PGMEA (480) | 10.8 | 0.18 | rectangular |
| I-23 | Polymer 2 (32) Polymer 4 (32) | PAG 2 (2) | DRR 7 (16) | TMEMEA (0.125) | PGMEA (480) | 10.5 | 0.18 | rectangular |
| I-24 | Polymer 5 (76) | PAG 7 (2) | DRR 4 (4) | TEA (0.125) | PGMEA (480) | 34.5 | 0.20 | T-top |
| I-25 | Polymer 5 (72) | PAG 7 (2) | DRR 4 (8) | TEA (0.125) | PGMEA (480) | 33.6 | 0.18 | slight T-top |
| I-26 | Polymer 5 (64) | PAG 7 (2) | DRR 4 (16) | TEA (0.125) | PGMEA (480) | 31.5 | 0.15 | rectangular |
| I-27 | Polymer 5 (56) | PAG 7 (2) | DRR 4 (24) | TEA (0.125) | PGMEA (480) | 30.9 | 0.18 | rectangular |
| I-28 | Polymer 6 (64) | PAG 8 (2) | DRR 5 (8) DRR 15 (8) | TEA (0.125) | PGMEA (480) | 13.5 | 0.20 | some positive taper |
| I-29 | Polymer 6 (64) | PAG 8 (2) | DRR 5 (8) DRR 16 (8) | TEA (0.125) | PGMEA (480) | 14.4 | 0.20 | some positive taper |
| I-30 | Polymer 6 (64) | PAG 8 (2) | DRR 5 (8) DRR 17 (8) | TEA (0.125) | PGMEA (480) | 12.9 | 0.20 | some positive taper |
| I-31 | Polymer 6 (64) | PAG 8 (2) | DRR 5 (8) DRR 18 (8) | TEA (0.125) | PGMEA (480) | 10.8 | 0.18 | rectangular |
| I-32 | Polymer 7 (64) | PAG 2 (2) | DRR 5 (16) | TEA (0.125) | PGMEA (480) | 18.0 | 0.18 | rectangular |
| I-33 | Polymer 7 (64) | PAG 2 (2) | DRR 5 (16) ACC 1 (4) | TEA (0.125) | PGMEA (480) | 17.4 | 0.15 | rectangular |
| I-34 | Polymer 8 (64) | PAG 2 (2) | DRR 5 (8) DRR 1 (8) | TEA (0.125) | PGMEA (480) | 19.5 | 0.18 | rectangular |
| I-35 | Polymer 8 (64) | PAG 2 (2) | DRR 5 (8) DRR 2 (8) | TEA (0.125) | PGMEA (480) | 18.9 | 0.18 | rectangular |

Comparative Examples I-1 to I-4

Resist materials were similarly formulated in accordance with the formulation shown in Table 3 and examined for performance. The composition and test results of the resist materials are shown in Table 3.

for 90 seconds, and developed with a solution of 2.38% tetramethylammonium hydroxide in water, thereby giving positive patterns.

The resulting resist patterns were evaluated as described below. First, the sensitivity (mJ/cm$^2$) was determined as the dose which provides a 1:1 resolution at the top and bottom

TABLE 3

| Comparative Example | Resin | Photoacid generator | Dissolution regulator | Basic compound | Solvent | Sensitivity | Resolution | shape |
|---|---|---|---|---|---|---|---|---|
| I-1 | Polymer 1 (64) | PAG 1 (2) | DRR 15 (16) | TBA (0.125) | PGMEA (480) | 44.5 | 0.22 | positive taper |
| I-2 | Polymer 1 (64) | PAG 1 (2) | DRR 16 (16) | TBA (0.125) | PGMEA (480) | 47.3 | 0.22 | positive taper |
| I-3 | Polymer 1 (64) | PAG 1 (2) | DRR 17 (16) | TBA (0.125) | PGMEA (480) | 43.1 | 0.22 | positive taper |
| I-4 | Polymer 1 (64) | PAG 1 (2) | DRR 18 (16) | TBA (0.125) | PGMEA (480) | 37.7 | 0.20 | rectangular |

Examples II-1 to II-20

Resist materials were formulated in accordance with the formulation shown in Table 4. These materials were each filtered through a 0.2-μm Teflon filter, thereby giving resist solutions. These resist solutions were spin-coated onto silicon wafers, then baked at 110° C. for 90 seconds on a hot plate to give resist films having a thickness of 0.7 μm. The resist films were exposed using a KrF excimer laser stepper (Nikon Corporation; NA 0.5), then baked (PEB) at 110° C.

of a 0.30 μm line-and-space pattern. The resolution of the resist under evaluation was defined as the minimum line width (μm) of the lines and spaces that separated at this dose. The shape of the resolved resist pattern was examined under a scanning electron microscope.

The composition and test results of the resist materials are shown in Table 4.

TABLE 4

| Example | Resin | Photoacid generator | Dissolution regulator | Basic compound | Solvent | Sensitivity | Resolution | shape |
|---|---|---|---|---|---|---|---|---|
| II-1 | Polymer 9 (64) | PAG 1 (2) | DRR 12 (16) | TEA (0.125) | PG/EL (480) | 42.3 | 0.22 | rectangular |
| II-2 | Polymer 9 (64) | PAG 1 (2) | DRR 13 (16) | TEA (0.125) | PG/EL (480) | 40.1 | 0.22 | rectangular |
| II-3 | Polymer 9 (64) | PAG 1 (2) | DRR 14 (16) | TEA (0.125) | PG/EL (480) | 38.5 | 0.22 | rectangular |
| II-4 | Polymer 9 (64) | PAG 2 (2) | DRR 13 (16) | TEA (0.125) | PG/EL (480) | 32.3 | 0.22 | rectangular |
| II-5 | Polymer 10 (64) | PAG 2 (2) | DRR 13 (16) | TEA (0.125) | PG/EL (480) | 33.5 | 0.22 | rectangular |
| II-6 | Polymer 11 (64) | PAG 2 (2) | DRR 13 (16) | TEA (0.125) | PG/EL (480) | 30.7 | 0.20 | rectangular |
| II-7 | Polymer 12 (64) | PAG 2 (2) | DRR 13 (16) | TEA (0.125) | PG/EL (480) | 31.2 | 0.22 | rectangular |
| II-8 | Polymer 10 (76) | PAG 4 (2) | DRR 14 (4) | TEA (0.125) | PGMEA (480) | 45.4 | 0.26 | T-top |
| II-9 | Polymer 10 (72) | PAG 4 (2) | DRR 14 (8) | TEA (0.125) | PGMEA (480) | 43.7 | 0.24 | slight T-top |
| II-10 | Polymer 10 (64) | PAG 4 (2) | DRR 14 (16) | TEA (0.125) | PGMEA (480) | 41.2 | 0.22 | rectangular |
| II-11 | Polymer 10 (56) | PAG 4 (2) | DRR 14 (24) | TEA (0.125) | PGMEA (480) | 40.7 | 0.22 | rectangular |
| II-12 | Polymer 9 (64) | PAG 5 (2) | DRR 13 (16) | TEA (0.125) | PGMEA (480) | 42.7 | 0.22 | rectangular |
| II-13 | Polymer 9 (64) | PAG 5 (2) | DRR 13 (8) DRR 12 (8) | TEA (0.125) | PGMEA (480) | 43.3 | 0.22 | rectangular |
| II-14 | Polymer 9 (64) | PAG 5 (2) | DRR 13 (8) DRR 14 (8) | TEA (0.125) | PGMEA (480) | 41.7 | 0.20 | rectangular |
| II-15 | Polymer 9 (64) | PAG 5 (2) | DRR 13 (8) DRR 15 (8) | TEA (0.125) | PGMEA (480) | 42.1 | 0.22 | rectangular |
| II-16 | Polymer 9 (64) | PAG 5 (2) | DRR 13 (8) DRR 16 (8) | TEA (0.125) | PGMEA (480) | 45.1 | 0.22 | rectangular |
| II-17 | Polymer 9 (64) | PAG 5 (2) | DRR 13 (8) DRR 17 (8) | TEA (0.125) | PGMEA (480) | 42.0 | 0.22 | rectangular |
| II-18 | Polymer 9 (64) | PAG 5 (2) | DRR 13 (8) DRR 18 (8) | TEA (0.125) | PGMEA (480) | 40.9 | 0.22 | rectangular |
| II-19 | Polymer 9 (64) | PAG 5 (2) | DRR 13 (16) ACC 1 (4) | TEA (0.125) | PGMEA (480) | 41.5 | 0.22 | rectangular |
| II-20 | Polymer 9 (64) | PAG 5 (2) | DRR 13 (16) ACC 2 (4) | TEA (0.125) | PGMEA (480) | 40.3 | 0.20 | rectangular |

Comparative Examples II-1 to II-4

Resist materials were similarly formulated in accordance with the formulation shown in Table 5 and examined for performance. The composition and test results of the resist materials are shown in Table 5.

TABLE 5

| Comparative Example | resin | Photoacid generator | Dissolution regulator | Basic compound | Solvent | Sensitivity | Resolution | shape |
|---|---|---|---|---|---|---|---|---|
| II-1 | Polymer 9 (64) | PAG 1 (2) | DRR 15 (16) | TEA (0.125) | PG/EL (480) | 45.9 | 0.26 | rectangular |
| II-2 | Polymer 9 (64) | PAG 1 (2) | DRR 16 (16) | TEA (0.125) | PG/EL (480) | 47.7 | 0.26 | some positive taper |
| II-3 | Polymer 9 (64) | PAG 1 (2) | DRR 17 (16) | TEA (0.125) | PG/EL (480) | 45.0 | 0.26 | rectangular |
| II-4 | Polymer 9 (64) | PAG 1 (2) | DRR 18 (16) | TEA (0.125) | PG/EL (480) | 44.5 | 0.26 | rectangular |

It is evident from Tables 1 to 5 that the resist materials within the scope of the invention show a higher sensitivity and resolution than the prior art resist materials.

Japanese Patent Application No. 11-138086 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A resist composition comprising an ester compound of formula 1:

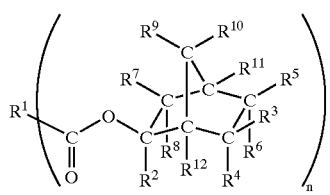

(1)

wherein

R$^1$ is an n-valent straight, branched or cyclic, saturated or unsaturated hydrocarbon group of 4 to 40 carbon atoms which optionally contain a hetero atom;

R$^2$ is a straight, branched or cyclic alkyl group of 1 to 8 carbon atoms or a substituted or unsubstituted aryl group of 6 to 20 carbon atoms;

R$^3$ to R$^{12}$ each are independently hydrogen or a monovalent hydrocarbon group of 1 to 15 carbon atoms wherein any two or more of R$^3$ to R$^6$, taken together, optionally and independently of each other form a ring, excluding a spiro ring, which are divalent hydrocarbon groups of 1 to 15 carbon atoms, or wherein two of R$^3$ to R$^{12}$ which are attached to adjacent carbon atoms optionally directly bond together to form a double bond; and n is an integer of 1 to 8, with the proviso that the formula also represents an enantiomer.

2. A resist composition of claim 1, further comprising a base resin, a photoacid generator, and an organic solvent.

3. A resist composition of claim 2, wherein the base resin is a polymer comprising one or more units of (R1) and/or (R2) and has a weight average molecular weight of about 1,000 to about 500,000;

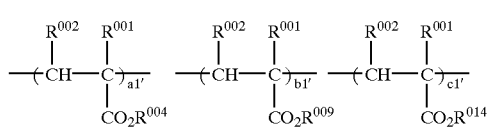

(R1)

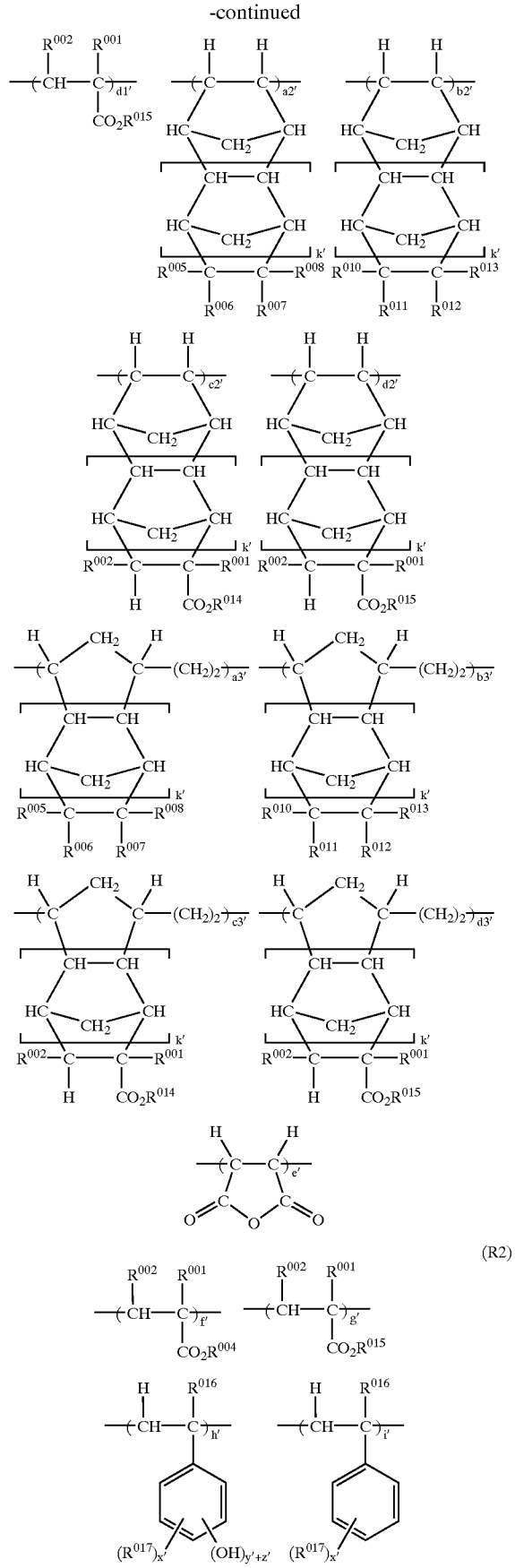

(R2)

-continued

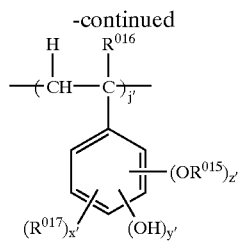

wherein, $R^{001}$ is hydrogen, methyl or $CH_2CO_2R^{003}$, $R^{002}$ is hydrogen, methyl or $CO_2R^{003}$, $R^{003}$ is a straight, branched or cyclic alkyl group of 1 to 15 carbon atoms, $R^{004}$ is hydrogen or a monovalent hydrocarbon group of 1 to 15 carbon atoms having a carboxyl or hydroxyl group, At least one of $R^{005}$ to $R^{008}$ is a monovalent hydrocarbon group of 1 to 15 carbon atoms having a carboxyl or hydroxyl group while the remaining R's independently represent hydrogen or a straight, branched or cyclic alkyl group of 1 to 15 carbon atoms, or $R^{005}$ to $R^{008}$, taken together, may form a ring, wherein at least one of $R^{005}$ to $R^{008}$ is a divalent hydrocarbon group of 1 to 15 carbon atoms having a carboxyl or hydroxyl group, while the remaining R's are independently straight, branched or cyclic alkylene groups of 1 to 15 carbon atoms, $R^{009}$ is a monovalent hydrocarbon group of 3 to 15 carbon atoms comprising a —$CO_2$— partial structure, At least one of $R^{010}$ to $R^{013}$ is a monovalent hydrocarbon group of 2 to 15 carbon atoms comprising a —$CO_2$— partial structure, while the remaining R's are independently hydrogen or straight, branched or cyclic alkyl groups of 1 to 15 carbon atoms, or $R^{010}$ to $R^{013}$, taken together, optionally form a ring, wherein at least one of $R^{010}$ to $R^{013}$ is a divalent hydrocarbon group of 1 to 15 carbon atoms containing a —$CO_2$— partial structure, while the remaining R's are independently straight, branched or cyclic alkylene groups of 1 to 15 carbon atoms, $R^{014}$ is a polycyclic hydrocarbon group having 7 to 15 carbon atoms or an alkyl group containing a polycylic hydrocarbon group, $R^{015}$ is an acid labile group, R016 is hydrogen or methyl, $R^{017}$ is a straight, branched or cyclic alkyl group of 1 to 8 carbon atoms, k' is 0 or 1;

a1', a2', a3', b1', b2', b3', c1', c2', c3', d1', d2', d3', and e' are numbers from 0 to 1, satisfying a1'+a2'+a3'+b1'+b2'+b3'+c1'+c2'+c3'+d1'+d2'+d3'=1; and f', g', h', i', and j' are numbers from 0 to less than 1, satisfying f'+g'+h'+i'+j'=1.

4. A resist composition of claim 2, which further comprises a dissolution regulator other than the ester compound of formula 1.

5. A resist composition of claim 2, which further comprises a basic compound.

6. A resist composition of claim 2, which further comprises a compound bearing

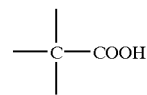

group.

7. A process for forming a pattern, comprising:

applying the resist composition of claim 1, onto a substrate to form a coating, heat treating the coating and exposing the coating to high energy radiation or electron radiation through a photomask, optionally heat treating the exposed coating, and optionally developing the coating with a developer.

8. A resist composition of claim 1, wherein the ester compound of formula 1 is:

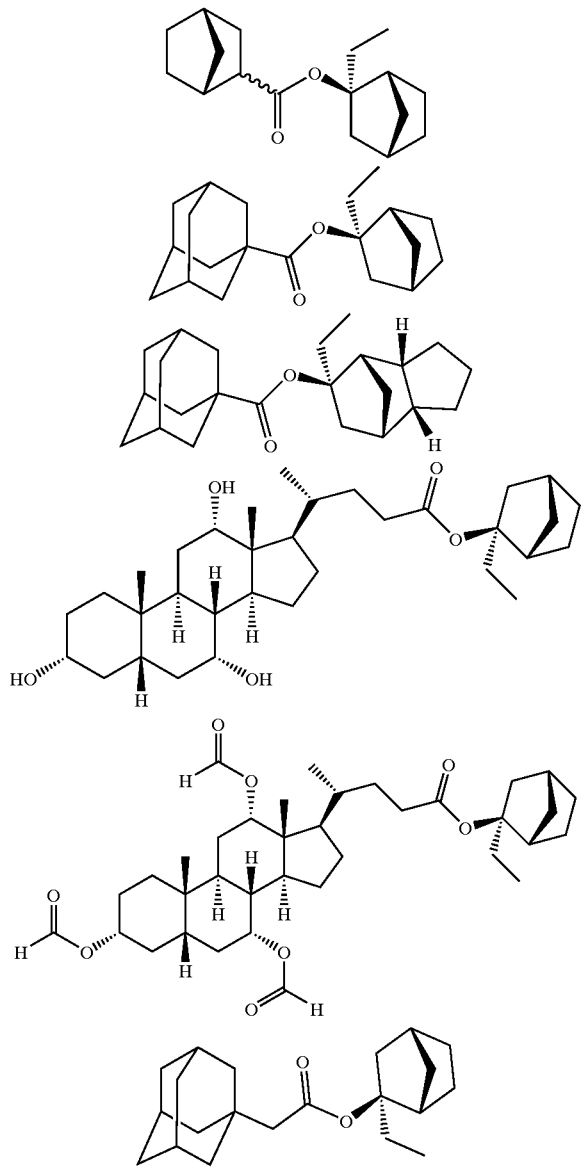

-continued

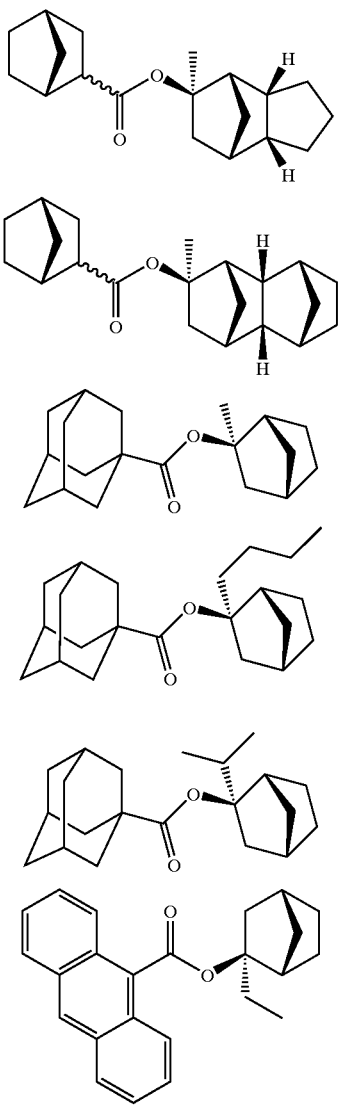

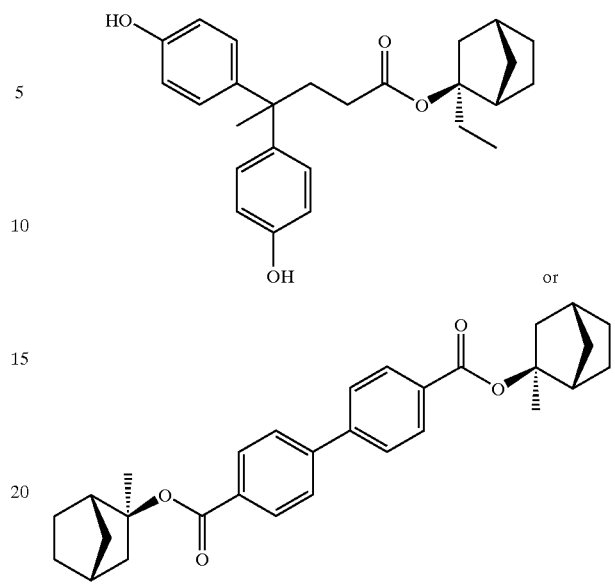

9. A resist composition comprising a compound of formula 1 of claim 1 which is in an exo-form.

10. A resist composition according to claim 9, wherein the exo-form compound of formula 1 is a dissolution regulator.

11. A resist composition comprising a compound according to claim 1 which is in an exo-form.

12. A resist composition according to claim 1, further comprising a base resin, a photoacid generator, and an organic solvent.

13. A resist composition according to claim 1, wherein the resist composition is positive working.

14. A resist composition according to claim 1, wherein the resist composition is negative working.

15. A resist composition according to claim 1, wherein the resist composition is positive and negative working.

* * * * *